United States Patent
Thornton et al.

(10) Patent No.: US 9,585,972 B2
(45) Date of Patent: Mar. 7, 2017

(54) METHOD FOR IMAGING A SITE OF ARTHRITIS IN AN ANIMAL

(76) Inventors: Sherry L. Thornton, Cincinnati, OH (US); Xiaoyang Qi, Cincinnati, OH (US); Matthew J. Flick, Cincinnati, OH (US)

( * ) Notice: Subject to any disclaimer, the term of this patent is extended or adjusted under 35 U.S.C. 154(b) by 0 days.

(21) Appl. No.: 14/116,711

(22) PCT Filed: May 9, 2012

(86) PCT No.: PCT/US2012/037085
§ 371 (c)(1),
(2), (4) Date: Nov. 8, 2013

(87) PCT Pub. No.: WO2012/154825
PCT Pub. Date: Nov. 15, 2012

(65) Prior Publication Data
US 2014/0086845 A1 Mar. 27, 2014

Related U.S. Application Data

(60) Provisional application No. 61/483,813, filed on May 9, 2011.

(51) Int. Cl.
| | | |
|---|---|---|
| A61B 5/00 | (2006.01) | |
| A61B 8/00 | (2006.01) | |
| A61B 10/00 | (2006.01) | |
| A61K 49/00 | (2006.01) | |
| A61K 9/51 | (2006.01) | |

(52) U.S. Cl.
CPC .......... *A61K 49/0056* (2013.01); *A61B 5/004* (2013.01); *A61B 5/0071* (2013.01); *A61B 5/4528* (2013.01); *A61B 2503/40* (2013.01); *A61K 9/5146* (2013.01); *A61K 49/0017* (2013.01)

(58) Field of Classification Search
USPC .......................................................... 424/9.6
See application file for complete search history.

(56) References Cited

U.S. PATENT DOCUMENTS

| 7,834,147 B2 | 11/2010 | Qi |
| 7,879,314 B2 | 2/2011 | Licha et al. |
| 2010/0144603 A1* | 6/2010 | Watnick ............................ 514/8 |

OTHER PUBLICATIONS

DeLay et al. (www.amnis.com/documents/posters/10-005-1-pos%20CYTO%202010%20Delay.pdf) May 11, 2010.*
Stolz et al. (Nature Nanotech. 2009, 4, 186-192).*
Post et al. (J. Nucl. Med. 2002, 43, 1359-1365).*
Schutters et al. (Apoptosis 2010, 15, 1072-1082).*
Balasubramanian et al., "Regulated externalization of phosphatidylserine at the cell surface: implications for apoptosis," J. Biol. Chem., Jun. 22, 2007, pp. 18357-18364, vol. 282(25).
Delay et al., "SapC-DOPS Agents in Imaging," Arthritis. Amnis CYTO 2010. Poster No. P207, May 11, 2010, Amnis Open House, Seattle, WA (https://www.amnis.com/documents/posters/10-005-1-pos%20CYTO%202010%20Delay.pdf).
Elliott et al., "Phosphatidylserine exposure in B lymphocytes: a role for lipid packing," Blood., Sep. 1, 2006, pp. 1611-1617, vol. 108(5).
Kaimal et al., "Saposin C coupled lipid nanovesicles enable cancer-selective optical and magnetic resonance imaging," Mol. Imaging Biol., Oct. 2011, pp. 886-897, vol. 13(5) [abstract only].
Latham et al., "Ex vivo characterization of the autoimmune T cell response in the HLA-DR1 mouse model of collagen-induced arthritis reveals long-term activation of type II collagen-specific cells and their presence in arthritic joints," J. Immunol., Apr. 1, 2005, pp. 3978-3985, vol. 174(7).
Qi et al., "Cancer-Selective Targeting and Cytotoxicity by Liposomal-Coupled Lysosomal Saposin C Protein," Clin. Cancer Res., Sep. 15, 2009, pp. 5840-5851, vol. 15.
Qi et al., "Differential membrane interactions of saposins A and C: implications for the functional specificity," J. Biol. Chem., Jul. 20, 2001, pp. 27010-27017, vol. 276(29).
Qi et al., "Saposin C coupled lipid nanovesicles specifically target arthritic mouse joints for optical imaging of disease severity," PLoS One, Mar. 2012, pp. e33966, vol. 7(3).
Stolz et al., "Early detection of aging cartilage and osteoarthritis in mice and patient samples using atomic force microscopy," Nature Nanotech., Mar. 2009, pp. 186-192, vol. 4 [abstract only].
Wunder et al., "Molecular imaging: novel tools in visualizing rheumatoid arthritis," Rheumatology, Nov. 2005, pp. 1341-1349, vol. 44(11).

* cited by examiner

*Primary Examiner* — Michael G Hartley
*Assistant Examiner* — Melissa Perreira
(74) *Attorney, Agent, or Firm* — Dinsmore & Shohl LLP

(57) ABSTRACT

The present disclosure demonstrates that a nanovesicle comprising a membrane-associated lysosomal protein (saposin C; "SapC") incorporated into a phospholipid has a high fusogenic affinity for phosphatidylserine-rich domains on the surfaces of target cell membranes. It is believed that the nanovesicles target surface exposed phosphatidylserine on the membranes of cells associated with arthritis, allowing for detection of local tissue damage associated with arthritis. In plasma membranes, phosphatidylserine is normally present only on the inner leaflet but is "flipped" to the outer leaflet upon the presence of cell damage. Incorporation of the fluorophore in the nanovesicles allows for the in vivo visualization of the fluorophore in targeted tissue and provides a technique to detect and evaluate the onset and progression of arthritic disease in an animal. Furthermore, the use of the nanovesicle in optical imaging methods provides great promise for analyzing events occurring early in the pathogenesis of arthritis and arthritic disease.

14 Claims, 17 Drawing Sheets

METHOD FOR IMAGING A SITE OF ARTHRITIS IN AN ANIMAL

CROSS-REFERENCE TO RELATED APPLICATIONS

The present application is a U.S. National Stage entry under 35 U.S.C. §371 of International Application No. PCT/US2012/037085, filed on May 9, 2012, designating the United States of America and published in English on Nov. 15, 2012, which in turn claims priority to U.S. Provisional Application No. 61/483,813, filed on May 9, 2011, each of which is hereby incorporated by reference in its entirety.

STATEMENT REGARDING FEDERALLY-SPONSORED RESEARCH

This invention was made with government support under grant numbers RR026314 and AR047363 awarded by the National Institutes of Health. The government has certain rights in the invention.

TECHNICAL FIELD

This invention pertains to the field of imaging a site of arthritis in an animal using a nanovesicle comprising a fluorophore, and methods for detection and assessment using the same.

BACKGROUND AND SUMMARY OF THE INVENTION

Arthritis is a joint disorder that involves inflammation of one or more joints. There are over 100 different forms of arthritis. The most common symptom of individuals affected with arthritis is joint pain. Arthritic pain is often constant and may be localized to the affected joint or joints. The pain from arthritis is typically associated with the inflammation that occurs around the joint, the damage to the joint resulting from arthritic disease, the daily wear and tear of the joint, the strain of muscles caused by forceful movements against stiff and painful joints, and fatigue. The direct costs of arthritis in the United States are estimated to be approximately $185.5 billion each year.

Rheumatoid arthritis is a debilitating type of arthritis that affects approximately 1% of the population. Rheumatoid arthritis is a chronic inflammatory disease in animals characterized by the destruction of cartilage and bone, frequently resulting in severe pain. Ultimately, untreated rheumatoid arthritis in patients can result in loss of joint function, reduction in quality of life, and, in extreme cases, morbidity.

The early detection and intervention of arthritis and arthritic disease are important for the successful treatment and preservation of joint mobility and function. For example, biological therapies for arthritis are most effective when they are used to intervene early in the disease process. However, reliable and manageable tools for evaluation of early joint inflammation and the onset and progression of arthritic disease are lacking. Furthermore, although radiographic imaging progression may be able to assess arthritic joint damage, soft tissue inflammation and destruction are not readily detected by radiography. A consensus has not been established for assessment of arthritic events involving inflammatory soft tissue with regard to imaging methods.

Therefore, there exists a need for a method to image a site of arthritis that overcomes the limitations of currently utilized evaluation methods in order to benefit the treatment of arthritis. Accordingly, the present disclosure provides methods of using a nanovesicle comprising a fluorophore which exhibits desirable properties and provides related advantages for the imaging of arthritis and arthritic disease.

The present disclosure demonstrates that a nanovesicle comprising a membrane-associated lysosomal protein (saposin C; "SapC") incorporated into a phospholipid has a high fusogenic affinity for phosphatidylserine-rich domains on the surfaces of target cell membranes. It is believed that the nanovesicles target surface-exposed phosphatidylserine on the membranes of cells associated with arthritis, allowing for detection of local tissue damage associated with arthritis. In plasma membranes, phosphatidylserine is normally present only on the inner leaflet but is "flipped" to the outer leaflet upon the presence of cell damage. Incorporation of the fluorophore in the nanovesicles allows for the in vivo visualization of the fluorophore in targeted tissue and provides a technique to detect and evaluate the onset and progression of arthritic disease in an animal. Furthermore, the use of the nanovesicle in optical imaging methods provides great promise for analyzing events occurring early in the pathogenesis of arthritis and arthritic disease.

Phosphatidylserine is present not only on cells undergoing apoptosis but also on cells that are injured. In addition, phosphatidylserine has been detected by Annexin V localization to cells that are stressed but not necessarily committed to apoptotic cell death (see Elliott, J. I. et al., "Phosphatidylserine exposure in B lymphocytes: a role for lipid packing," *Blood,* 2006; 108:1611-1617; and Balasubramanian, K. et al., "Regulated externalization of phosphatidylserine at the cell surface: implications for apoptosis," *J Biol Chem,* 2007; 282:18357-18364). Thus, it has been suggested that binding to phosphatidylserine may identify tissues or organs at risk for irreversible injury. In particular, studies of a Collagen-Induced Arthritis (CIA) mouse model using $^{99mTc}$-Annexin V, a composition with a high affinity for phosphatidylserine, detected the presence and amount of apoptosis in peripheral joints of arthritic mice using radiographic analysis (see Post, A. M. et al., "Imaging cell death with radiolabeled annexin V in an experimental model of rheumatoid arthritis," *J Nucl Med,* 2002; 43:1359-1365). Thus, the described methods, which utilize a nanovesicle that localizes to cells involved in inflammation and injury in arthritis, provide a valuable tool for the early assessment of arthritic disease and progression of arthritic disease.

The present disclosure describes several advantages compared to current methods utilized for the imaging, detection, and assessment of arthritis in an animal. For instance, embodiments of the present disclosure can be applied via optical imaging, which uses probes that, when excited, emit light that can penetrate the skin more readily than probes with lower emission wavelengths. Thus, the use of optical imaging can facilitate advantageous signal detection in vivo. Some advantages of optical imaging include a decrease in radiation exposure compared to X-ray imaging, a clear targeting and localization of molecular probes associated with disease pathogenesis, and a minimal acquisition time compared to other radiographic methods.

Furthermore, embodiments of the present disclosure can specifically target damaged tissue to enhance imaging of inflammation associated with arthritis. The described nanovesicles comprise a fusogenic protein, saposin C, incorporated into a phospholipid. Saposin C associates with phosphatidylserine on cell membranes by embedding amino and carboxyl-end amphipathic helices into the outer leaflet of membranes (see Qi, X. et al., "Differential membrane interactions of saposins A and C: implications for the functional specificity," *J Biol Chem,* 2001; 276:27010-27017).

The following numbered embodiments are contemplated and are non-limiting:

1. A method for imaging a site of arthritis in an animal, the method comprising the step of administering to the animal a nanovesicle comprising saposin C, 1,2-dioleoyl-sn-glycero-3-phospho-L-serine (DOPS), and a fluorophore,
wherein the site of arthritis is detected by imaging a population of cells at the site of arthritis.

2. The method of clause 1, wherein the arthritis is an inflammatory arthritis.

3. The method of clause 1, wherein the arthritis is selected from the group consisting of rheumatoid arthritis, osteoarthritis, psoriatic arthritis, traumatic arthritis, bacterial arthritis, post-infectious arthritis, lyme disease (Borreliose), anklyosing spondylilitis, and rubella arthritis.

4. The method of clause 1, wherein the arthritis is rheumatoid arthritis.

5. The method of clause 1, wherein the arthritis is osteoarthritis.

6. The method of any one of clauses 1 to 5, wherein the imaging is optical imaging.

7. The method of any one of clauses 1 to 6, wherein the animal is a mammal.

8. The method of any one of clauses 1 to 7, wherein the animal is a human.

9. The method of any one of clauses 1 to 8, wherein the fluorophore is a near-red fluorophore or an infrared fluorophore.

10. The method of any one of clauses 1 to 8, wherein the fluorophore is selected from the group consisting of CellVue® Maroon (Ex max=647 nm and Em max=667 nm), CellVue® Claret (Ex max=655 nm and Em max=675 nm), CellVue® Plum (Ex max=652 nm and Em max=671 nm), CellVue® Burgundy (Ex max=683 nm and Em max=707 nm), CellVue® Lavendar (Ex max=420 nm and Em max=461 nm), CellVue® NIR815 (Ex max=786 nm and Em max=814 nm), CellVue® NIR780 (Abs max=745 nm and Em max=776 nm), CellVue® Jade (Abs max=478 nm and Em max=508 nm), and CellVue® Red (Ex max=567 nm and Em max=588 nm).

11. The method of any one of clauses 1 to 8, wherein the fluorophore is CellVue® Maroon (CVM).

12. The method of any one of clauses 1 to 8, wherein the fluorophore is CellVue® Claret.

13. The method of any one of clauses 1 to 8, wherein the fluorophore is CellVue® Plum.

14. The method of any one of clauses 1 to 8, wherein the fluorophore is CellVue® Burgundy.

15. The method of any one of clauses 1 to 8, wherein the fluorophore is CellVue® Lavendar.

16. The method of any one of clauses 1 to 8, wherein the fluorophore is CellVue® NIR815.

17. The method of any one of clauses 1 to 8, wherein the fluorophore is CellVue® NIR780.

18. The method of any one of clauses 1 to 8, wherein the fluorophore is CellVue® Jade.

19. The method of any one of clauses 1 to 8, wherein the fluorophore is CellVue® Red.

20. The method of any one of clauses 1 to 19, wherein the site of arthritis is selected from the group consisting of hand, foot, knee, elbow, shoulder, hip, and sacroiliac joint.

21. The method of any one of clauses 1 to 11, wherein the site of arthritis is an arthritic joint tissue.

22. The method of any one of clauses 1 to 20, wherein the site of arthritis is a joint.

23. The method of clause 22, wherein the joint is selected from the group consisting of wrist, knee, elbow, forefoot, ankle, subtalar, and synovial joints.

24. The method of any one of clauses 1 to 23, wherein the cells are inflammatory cells.

25. The method of any one of clauses 1 to 24, wherein the cells include an externalized phosphatidylserine on the membrane of the cells.

26. The method of any one of clauses 1 to 25, wherein the cells are associated with arthritis.

27. The method of any one of clauses 1 to 26, wherein the cells are selected from the group consisting of lymphocytes, macrophages, T cells, B cells, natural killer (NK) cells, myeloid cells, fibroblasts, synovial fibroblasts, endothelial cells, mature granulocytes, and neutrophils.

28. The method of any one of clauses 1 to 27, wherein the cells are neutrophils.

29. The method of any one of clauses 1 to 28, wherein the cells express a cell surface marker selected from the group consisting of CD11b, CD19, GR-1, CD31, CD55, and F480.

30. The method of any one of clauses 1 to 29, wherein the cell surface marker is CD11b.

31. The method of any one of clauses 1 to 29, wherein the cell surface marker is CD19.

32. The method of any one of clauses 1 to 29, wherein the cell surface marker is Gr-1.

33. The method of any one of clauses 1 to 29, wherein the cell surface marker is CD31.

34. The method of any one of clauses 1 to 29, wherein the cell surface marker is CD55

35. The method of any one of clauses 1 to 29, wherein the cell surface marker is F480.

36. The method of any one of clauses 1 to 29, wherein the cells are positive for both CD11b and Gr-1.

37. A method for detecting early onset of arthritis in an animal, the method comprising the step of administering to the animal a nanovesicle comprising saposin C, 1,2-dioleoyl-sn-glycero-3-phospho-L-serine (DOPS), and a fluorophore,
wherein a site of arthritis is detected by imaging a population of cells at the site of arthritis, and
wherein the detection of early onset of arthritis is obtained from the imaging of the population of cells.

38. The method of clause 37, wherein the arthritis is an inflammatory arthritis.

39. The method of clause 37, wherein the arthritis is selected from the group consisting of rheumatoid arthritis, osteoarthritis, psoriatic arthritis, traumatic arthritis, bacterial arthritis, post-infectious arthritis, lyme disease (Borreliose), anklyosing spondylilitis, and rubella arthritis.

40. The method of clause 37, wherein the arthritis is rheumatoid arthritis.

41. The method of clause 37, wherein the arthritis is osteoarthritis.

42. The method of any one of clauses 37 to 41, wherein the imaging is optical imaging.

43. The method of any one of clauses 37 to 42, wherein the animal is a mammal.

44. The method of any one of clauses 37 to 43, wherein the animal is a human.

45. The method of any one of clauses 37 to 44, wherein the fluorophore is a near-red fluorophore or an infrared fluorophore.

46. The method of any one of clauses 37 to 44, wherein the fluorophore is selected from the group consisting of CellVue® Maroon (Ex max=647 nm and Em max=667 nm), CellVue® Claret (Ex max=655 nm and Em max=675 nm), CellVue® Plum (Ex max=652 nm and Em max=671 nm), CellVue® Burgundy (Ex max=683 nm and Em max=707 nm), CellVue® Lavendar (Ex max=420 nm and Em max=461 nm), CellVue® NIR815 (Ex max=786 nm and Em max=814 nm), CellVue® NIR780 (Abs max=745 nm and Em max=776 nm), CellVue® Jade (Abs max=478 nm and Em max=508 nm), and CellVue® Red (Ex max=567 nm and Em max=588 nm).

47. The method of any one of clauses 37 to 44, wherein the fluorophore is CellVue® Maroon (CVM).

48. The method of any one of clauses 37 to 44, wherein the fluorophore is CellVue® Claret.

49. The method of any one of clauses 37 to 44, wherein the fluorophore is CellVue® Plum.

50. The method of any one of clauses 37 to 44, wherein the fluorophore is CellVue® Burgundy.

51. The method of any one of clauses 37 to 44, wherein the fluorophore is CellVue® Lavendar.

52. The method of any one of clauses 37 to 44, wherein the fluorophore is CellVue® NIR815.

53. The method of any one of clauses 37 to 44, wherein the fluorophore is CellVue® NIR780.

54. The method of any one of clauses 37 to 44, wherein the fluorophore is CellVue® Jade.

55. The method of any one of clauses 37 to 44, wherein the fluorophore is CellVue® Red.

56. The method of any one of clauses 37 to 55, wherein the site of arthritis is selected from the group consisting of hand, foot, knee, elbow, shoulder, hip, and sacroiliac joint.

57. The method of any one of clauses 37 to 56, wherein the site of arthritis is an arthritic joint tissue.

58. The method of any one of clauses 37 to 57, wherein the site of arthritis is a joint.

59. The method of clause 58, wherein the joint is selected from the group consisting of wrist, knee, elbow, forefoot, ankle, subtalar, and synovial joints.

60. The method of any one of clauses 37 to 59, wherein the cells are inflammatory cells.

61. The method of any one of clauses 37 to 60, wherein the cells include an externalized phosphatidylserine on the membrane of the cells.

62. The method of any one of clauses 37 to 61, wherein the cells are associated with arthritis.

63. The method of any one of clauses 37 to 62, wherein the cells are selected from the group consisting of lymphocytes, macrophages, T cells, B cells, natural killer (NK) cells, myeloid cells, fibroblasts, synovial fibroblasts, endothelial cells, mature granulocytes, and neutrophils.

64. The method of any one of clauses 37 to 63, wherein the cells are neutrophils.

65. The method of any one of clauses 37 to 64, wherein the cells express a cell surface marker selected from the group consisting of CD11b, CD19, GR-1, CD31, CD55, and F480.

66. The method of any one of clauses 37 to 65, wherein the cell surface marker is CD11b.

67. The method of any one of clauses 37 to 65, wherein the cell surface marker is CD19.

68. The method of any one of clauses 37 to 65, wherein the cell surface marker is Gr-1.

69. The method of any one of clauses 37 to 65, wherein the cell surface marker is CD31.

70. The method of any one of clauses 37 to 65, wherein the cell surface marker is CD55.

71. The method of any one of clauses 37 to 65, wherein the cell surface marker is F480

72. The method of any one of clauses 37 to 65, wherein the cells are positive for both CD11b and Gr-1.

73. A method for assessing disease progression of arthritis in an animal, the method comprising the step of administering to the animal a nanovesicle comprising saposin C, 1,2-dioleoyl-sn-glycero-3-phospho-L-serine (DOPS), and a fluorophore,
wherein a site of arthritis is detected by imaging a population of cells at the site of arthritis, and
wherein the assessment of disease progression of arthritis is obtained from the imaging of the population of cells.

74. The method of clause 73, wherein the arthritis is an inflammatory arthritis.

75. The method of clause 73, wherein the arthritis is selected from the group consisting of rheumatoid arthritis, osteoarthritis, psoriatic arthritis, traumatic arthritis, bacterial arthritis, post-infectious arthritis, lyme disease (Borreliose), anklyosing spondylilitis, and rubella arthritis.

76. The method of clause 73, wherein the arthritis is rheumatoid arthritis.

77. The method of clause 73, wherein the arthritis is osteoarthritis.

78. The method of any one of clauses 73 to 77, wherein the imaging is optical imaging.

79. The method of any one of clauses 73 to 78, wherein the animal is a mammal.

80. The method of any one of clauses 73 to 79, wherein the animal is a human.

81. The method of any one of clauses 73 to 80, wherein the fluorophore is a near-red fluorophore or an infrared fluorophore.

82. The method of any one of clauses 73 to 80, wherein the fluorophore is selected from the group consisting of CellVue® Maroon (Ex max=647 nm and Em max=667 nm), CellVue® Claret (Ex max=655 nm and Em max=675 nm), CellVue® Plum (Ex max=652 nm and Em max=671 nm), CellVue® Burgundy (Ex max=683 nm and Em max=707 nm), CellVue® Lavendar (Ex max=420 nm and Em max=461 nm), CellVue® NIR815 (Ex max=786 nm and Em max=814 nm), CellVue® NIR780 (Abs max=745 nm and Em max=776 nm), CellVue® Jade (Abs max=478 nm and Em max=508 nm), and CellVue® Red (Ex max=567 nm and Em max=588 nm).

83. The method of any one of clauses 73 to 80, wherein the fluorophore is CellVue® Maroon (CVM).

84. The method of any one of clauses 73 to 80, wherein the fluorophore is CellVue® Claret.

85. The method of any one of clauses 73 to 80, wherein the fluorophore is CellVue® Plum.

86. The method of any one of clauses 73 to 80, wherein the fluorophore is CellVue® Burgundy.

87. The method of any one of clauses 73 to 80, wherein the fluorophore is CellVue® Lavendar.

88. The method of any one of clauses 73 to 80, wherein the fluorophore is CellVue® NIR815.

89. The method of any one of clauses 73 to 80, wherein the fluorophore is CellVue® NIR780.

90. The method of any one of clauses 73 to 80, wherein the fluorophore is CellVue® Jade.

91. The method of any one of clauses 73 to 80, wherein the fluorophore is CellVue® Red.

92. The method of any one of clauses 73 to 91, wherein the site of arthritis is selected from the group consisting of hand, foot, knee, elbow, shoulder, hip, and sacroiliac joint.

93. The method of any one of clauses 73 to 92, wherein the site of arthritis is an arthritic joint tissue.

94. The method of any one of clauses 73 to 93, wherein the site of arthritis is a joint.

95. The method of clause 94, wherein the joint is selected from the group consisting of wrist, knee, elbow, forefoot, ankle, subtalar, and synovial joints.

96. The method of any one of clauses 73 to 95, wherein the cells are inflammatory cells.

97. The method of any one of clauses 73 to 96, wherein the cells include an externalized phosphatidylserine on the membrane of the cells.

98. The method of any one of clauses 73 to 97, wherein the cells are associated with arthritis.

99. The method of any one of clauses 73 to 98, wherein the cells are selected from the group consisting of lymphocytes, macrophages, T cells, B cells, natural killer (NK) cells, myeloid cells, fibroblasts, synovial fibroblasts, endothelial cells, mature granulocytes, and neutrophils.

100. The method of any one of clauses 73 to 99, wherein the cells are neutrophils.

101. The method of any one of clauses 73 to 100, wherein the cells express a cell surface marker selected from the group consisting of CD11b, CD19, GR-1, CD31, CD55, and F480.

102. The method of any one of clauses 73 to 101, wherein the cell surface marker is CD11b.

103. The method of any one of clauses 73 to 101, wherein the cell surface marker is CD19.

104. The method of any one of clauses 73 to 101, wherein the cell surface marker is Gr-1.

105. The method of any one of clauses 73 to 101, wherein the cell surface marker is CD31.

106. The method of any one of clauses 73 to 101, wherein the cell surface marker is CD55.

107. The method of any one of clauses 73 to 101, wherein the cell surface marker is F480

108. The method of any one of clauses 73 to 101, wherein the cells are positive for both CD11b and Gr-1.

109. The method of any one of clauses 73 to 108, wherein the assessment of disease progression of arthritis is used to determine arthritis treatment for the animal.

110. The method of any one of clauses 73 to 109, wherein the assessment of disease progression of arthritis is used to monitor therapeutic response of arthritis treatment to the animal.

111. A method for assessing inflammation of a joint in an animal, the method comprising the step of administering to the animal a nanovesicle comprising saposin C, 1,2-dioleoyl-sn-glycero-3-phospho-L-serine (DOPS), and a fluorophore,
wherein the inflammation of the joint is detected by imaging a population of cells at the joint, and
wherein the assessment of inflammation is obtained from the imaging of the population of cells.

112. The method of clause 111, wherein the inflammation of the joint is associated with arthritis.

113. The method of clause 112, wherein the arthritis is selected from the group consisting of rheumatoid arthritis, osteoarthritis, psoriatic arthritis, traumatic arthritis, bacterial arthritis, post-infectious arthritis, lyme disease (Borreliose), anklyosing spondylilitis, and rubella arthritis.

114. The method of clause 112, wherein the arthritis is rheumatoid arthritis.

115. The method of clause 112, wherein the arthritis is osteoarthritis.

116. The method of any one of clauses 111 to 115, wherein the imaging is optical imaging.

117. The method of any one of clauses 111 to 116, wherein the animal is a mammal.

118. The method of any one of clauses 111 to 117, wherein the animal is a human.

119. The method of any one of clauses 111 to 118, wherein the fluorophore is a near-red fluorophore or an infrared fluorophore.

120. The method of any one of clauses 111 to 118, wherein the fluorophore is selected from the group consisting of CellVue® Maroon (Ex max=647 nm and Em max=667 nm), CellVue® Claret (Ex max=655 nm and Em max=675 nm), CellVue® Plum (Ex max=652 nm and Em max=671 nm), CellVue® Burgundy (Ex max=683 nm and Em max=707 nm), CellVue® Lavendar (Ex max=420 nm and Em max=461 nm), CellVue® NIR815 (Ex max=786 nm and Em max=814 nm), CellVue® NIR780 (Abs max=745 nm and Em max=776 nm), CellVue® Jade (Abs max=478 nm and Em max=508 nm), and CellVue® Red (Ex max=567 nm and Em max=588 nm).

121. The method of any one of clauses 111 to 118, wherein the fluorophore is CellVue® Maroon (CVM).

122. The method of any one of clauses 111 to 118, wherein the fluorophore is CellVue® Claret.

123. The method of any one of clauses 111 to 118, wherein the fluorophore is CellVue® Plum.

124. The method of any one of clauses 111 to 118, wherein the fluorophore is CellVue® Burgundy.

125. The method of any one of clauses 111 to 118, wherein the fluorophore is CellVue® Lavendar.

126. The method of any one of clauses 111 to 118, wherein the fluorophore is CellVue® NIR815.

127. The method of any one of clauses 111 to 118, wherein the fluorophore is CellVue® NIR780.

128. The method of any one of clauses 111 to 118, wherein the fluorophore is CellVue® Jade.

129. The method of any one of clauses 111 to 118, wherein the fluorophore is CellVue® Red.

130. The method of any one of clauses 111 to 129, wherein the cells include an externalized phosphatidylserine on the membrane of the cells.

131. The method of any one of clauses 111 to 130, wherein the cells are associated with arthritis.

132. The method of any one of clauses 111 to 131, wherein the cells are selected from the group consisting of lymphocytes, macrophages, T cells, B cells, natural killer (NK) cells, myeloid cells, fibroblasts, synovial fibroblasts, endothelial cells, mature granulocytes, and neutrophils.

133. The method of any one of clauses 111 to 132, wherein the cells are neutrophils.

134. The method of any one of clauses 111 to 133, wherein the cells express a cell surface marker selected from the group consisting of CD11b, CD19, GR-1, CD31, CD55, and F480.

135. The method of any one of clauses 111 to 134, wherein the cell surface marker is CD11b.

136. The method of any one of clauses 111 to 134, wherein the cell surface marker is CD19.

137. The method of any one of clauses 111 to 134, wherein the cell surface marker is Gr-1.

138. The method of any one of clauses 111 to 134, wherein the cell surface marker is CD31.

139. The method of any one of clauses 111 to 134, wherein the cell surface marker is CD55

140. The method of any one of clauses 111 to 134, wherein the cell surface marker is F480.

141. The method of any one of clauses 111 to 134, wherein the cells are positive for both CD11b and Gr-1.

142. The method of any one of clauses 111 to 141, wherein the assessment of inflammation is used to determine arthritis treatment for the animal.

143. The method of any one of clauses 111 to 142, wherein the assessment of inflammation is used to monitor therapeutic response of arthritis treatment to the animal.

DETAILED DESCRIPTION OF THE ILLUSTRATIVE EMBODIMENTS

Figure 1:
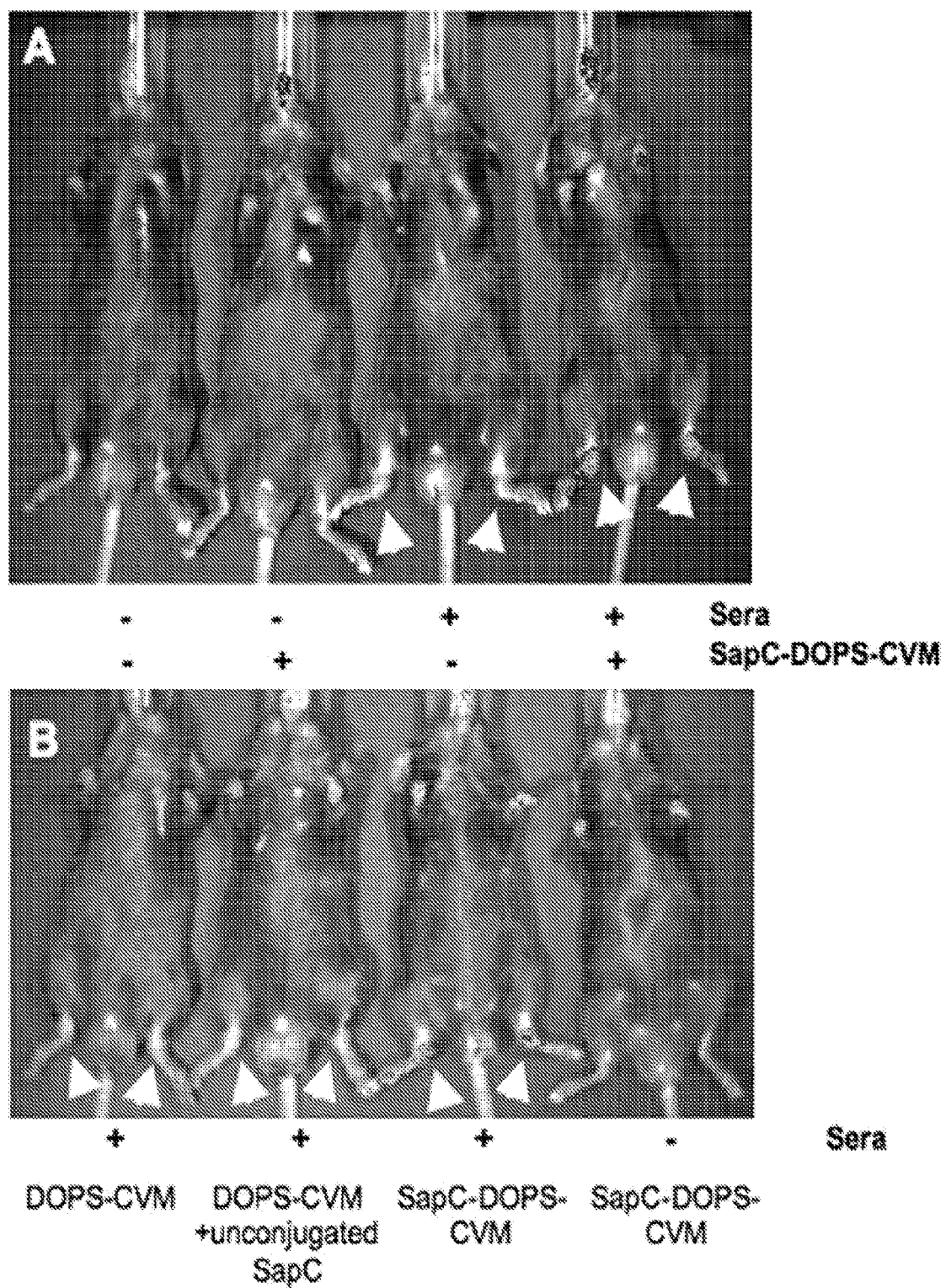
FIG. 1 shows that nanovesicles labeled with CellVue® Maroon (CVM) localize to arthritic joints and are visible by fluorometric imaging. Male C57Bl/6 mice (three months of age) were administered 150 microliters (µL) of sera i.p. as indicated. Seven days after sera injection, mice were imaged by IVIS® at: (A) five hours following i.v. injection of a saposin C/dioleoylphosphatidylserine/CellVue® Maroon (SapC-DOPS-CVM) nanovesicle as indicated (+/− indicates the presence or absence of PBS, respectively); (B) two hours following i.v. injection of either DOPS-CVM, DOPS-CVM plus unconjugated SapC, or SapC-DOPS-CVM as indicated. Arrows indicate macroscopically swollen paws.

Various embodiments of the invention are described herein as follows. In one embodiment described herein, a method for imaging a site of arthritis in an animal is provided. The method comprises the step of administering to the animal a nanovesicle comprising saposin C, a phospholipid, and a fluorophore, and wherein the site of arthritis is detected by imaging a population of cells at the site of arthritis.

In another illustrative embodiment described herein, a method for detecting early onset of arthritis in an animal is provided. The method comprises the step of administering to the animal a nanovesicle comprising saposin C, a phospholipid, and a fluorophore, wherein a site of arthritis is detected by imaging a population of cells at the site of arthritis, and wherein the detection of early onset of arthritis is obtained from the imaging of the population of cells.

In yet another illustrative embodiment, a method for assessing disease progression of arthritis in an animal is provided. The method comprises the step of administering to the animal a nanovesicle comprising saposin C, a phospholipid, and a fluorophore, wherein a site of arthritis is detected by imaging a population of cells at the site of arthritis, and wherein the assessment of disease progression of arthritis is obtained from the imaging of the population of cells.

In another illustrative embodiment, a method for assessing inflammation of a joint in an animal is provided. The method comprises the step of administering to the animal a nanovesicle comprising saposin C, a phospholipid, and a fluorophore, wherein the inflammation of the joint is detected by imaging a population of cells at the joint, and wherein the assessment of inflammation is obtained from the imaging of the population of cells.

In the various embodiments, the nanovesicle comprises saposin C, a phospholipid, and a fluorophore. The nanoparticles can be formed using any available process or method known in the art. As used herein, the term "saposin C" refers to a membrane-associated lysosomal protein that is well known to one of skill in the art. Saposin C is a fusogenic polypeptide that, when added to two separate bilayer membranes, can bring about fusion of the membranes into a single membrane. The saposin C polypeptide has the following sequence (SEQ ID NO:1):

```
Ser Asp Val Tyr Cys Glu Val Cys Glu Phe

Leu Val Lys Glu Val Thr Lys Leu Ile Asp

Asn Asn Lys Thr Glu Lys Glu Ile Leu Asp

Ala Phe Asp Lys Met Cys Ser Lys Leu Pro

Lys Ser Leu Ser Glu Glu Cys Gln Glu Val

Val Asp Thr Tyr Gly Ser Ser Ile Leu Ser

Ile Leu Leu Glu Glu Val Ser Pro Glu Leu

Val Cys Ser Met Leu His Leu Cys Ser Gly
```

In other embodiments, the saposin C polypeptide comprises an amino acid sequence with 80%, 85%, 90%, 95%, 98%, or 100% homology to SEQ ID NO: 1.

In various embodiments, the saposin C polypeptide described herein can be modified by the inclusion of one or more conservative amino acid substitutions. As is well-known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions are possible provided that these do not excessively affect the fusogenic activity of the saposin C polypeptide.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in TABLE 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

As used herein, the term "phospholipid" refers to any of a group of fatty compounds comprising phosphoric esters. For example, the phospholipid can be selected from the group consisting of fatty acids, lysolipids, phosphatidylcholines, phosphatidylethanolamines, phosphatidylserines, phosphatidylglycerols, phosphatidylinositols, sphingolipids, glycolipids, glucolipids, sulfatides, glycosphingolipids, phosphatidic acids, palmitic acids, stearic acids, arachidonic acids, oleic acids, lipids bearing polymers, lipids bearing sulfonated monosaccharides, lipids bearing sulfonated disaccharides, lipids bearing sulfonated oligosaccharides, lipids bearing sulfonated polysaccharides, cholesterols, tocopherols, lipids with ether-linked fatty acids, lipids with ester-linked fatty acids, polymerized lipids, diacetyl phosphates, dicetyl phosphates, stearylamines, cardiolipin, phospholipids with fatty acids of 6-8 carbons in length, synthetic phospholipids with asymmetric acyl chains, ceramides, non-ionic lipids, sterol aliphatic acid esters, sterol esters of sugar acids, esters of sugar acids, esters of sugar alcohols, esters of sugars, esters of aliphatic acids, saponins, glycerol dilaurate, glycerol trilaurate, glycerol dipalmitate, glycerol, glycerol esters, alcohols of 10-30 carbons in length, 6-(5- cholesten-3beta-yloxy)-1-thio-beta-D-galactopyranoside, digalactosyldiglyceride, 6-(5-cholesten-3beta-yloxy)hexyl-6-amino-6-deoxy-1-thio-beta-D-galacto pyranoside, 6-(5-cholesten-3beta-yloxy)hexyl-6-amino-6-deoxyl-1-thio-alpha-D-manno pyranoside, 12-(((7'-diethylaminocoumarin-3-yl)carbonyl)methylamino)-octalecanoic acid, N-[12-(((7'-diethylaminocoumarin-3-yl)carbonyl)methylamino) octadeca-noyl]-2-aminopalimitic acid, cholesteryl(4'-trimethylammonio)butanoate, N-succinyldioleoylphosphatidylethanol-amine, 1,2-dioleoyl-sn-glycerol, 1,2-dipalmitoyl-sn-3-succinylglycerol, 1,3-dipalmitoyl-2-succinylglycerol, 1-hexadecyl-2-palmitoylglycerophosphoethanolamine, palmitoylhomocysteine, cationic lipids, N-[1-(2,3-dioleoyloxy)propyl]-N,N,N-trimethylammoium chloride, 1,2-dioleoyloxy-3-(trimethylammonio)propane, 1,2-dioleoyl-3-(4'-trimethylammonio)butanoyl-sn-glycerol, lysophospholipids, lysobisphosphatidic acid (LBPA), semi-lysobisphosphatidic acid (semi-LBPA), cardiolipin, lipids bearing cationic polymers, alkyl phosphonates, alkyl phosphinates, and alkyl phosphites. In one embodiment, the phosphatidylcholine is selected from the group consisting of dioleoylphosphatidylcholine, dimyristoylphosphatidylcholine, dipentadecanoylphosphatidylcholine, dilauroylphosphatidylcholine, dipalmitoylphosphatidylcholine, and distearoylphosphatidylcholine; wherein the phosphatidylethanolamine is selected from the group consisting of dipalmitoylphosphatidylethanolamine and dioleoylphosphatidylethanolamine; wherein the sphingolipid is sphingomyelin; wherein the glycolipid is selected from the group consisting of ganglioside GM1 and ganglioside GM2; wherein in the lipids bearing polymers the polymer is selected from the group consisting of polyethyleneglycol, chitin, hyaluronic acid and polyvinylpyrrolidone; wherein the sterol aliphatic acid esters are selected from the group consisting of cholesterol sulfate, cholesterol butyrate, cholesterol isobutyrate, cholesterol palmitate, cholesterol stearate, lanosterol acetate, ergosterol palmitate, and phytosterol n-butyrate; wherein the sterol esters of sugar acids are selected from the group consisting of cholesterol glucuronide, lanosterol glucuronide, 7-dehydrocholesterol glucuronide, ergosterol glucuronide, cholesterol gluconate, lanosterol gluconate, and ergosterol gluconate; wherein the esters of sugar acids and the esters of sugar alcohols are selected from the group consisting of lauryl glucuronide, stearoyl glucuronide, myristoyl glucuronide, lauryl gluconate, myristoyl gluconate, and stearoyl gluconate; wherein the esters of sugars and the esters of aliphatic acids are selected from the group consisting of sucrose laurate, fructose laurate, sucrose palmitate, sucrose stearate, glucuronic acid, gluconic acid, accharic acid, and polyuronic acid; wherein the saponins are selected from the group consisting of sarsasapogenin, smilagenin, hederagenin, oleanolic acid, and digitoxigenin; wherein the glycerol esters are selected from the group consisting of glycerol tripalmitate, glycerol distearate, glycerol tristearate, glycerol dimyristate, glycerol and trimyristate; wherein the alcohols are of 10-30 carbon length and are selected from the group consisting of n-decyl alcohol, lauryl alcohol, myristyl alcohol, cetyl alcohol, and n-octadecyl alcohol; wherein in the lipids bearing cationic polymers the cationic polymers are selected from the group consisting of polylysine and polyarginine.

In another embodiment, the phospholipid is selected from the group consisting of dipalmitoylphosphatidylcholine, dipalmitoylphosphatidylethanolamine, and dipalmitoylphosphatidic acid, and structural analogs thereof. In one embodiment, the phospholipid is dioleoylphosphatidylserine (1,2-dioleoyl-sn-glycero-3-phospho-L-serine; "DOPS").

As used herein, the term "fluorophore" is defined as a molecule/compound that exhibits fluorescence. In some embodiments, the fluorophore has a wavelength range of approximately 600-1000 nm. In one embodiment, the fluorophore is a far-red fluorophore. In another embodiment, the fluorophore is a near-infrared fluorophore.

In some embodiments, the fluorophore is selected from the group consisting of CellVue® Maroon (Ex max=647 nm and Em max=667 nm), CellVue® Claret (Ex max=655 nm and Em max=675 nm), CellVue® Plum (Ex max=652 nm and Em max=671 nm), CellVue® Burgundy (Ex max=683 nm and Em max=707 nm), CellVue® Lavendar (Ex max=420 nm and Em max=461 nm), CellVue® NIR815 (Ex max=786 nm and Em max=814 nm), CellVue® NIR780 (Abs max=745 nm and Em max=776 nm), CellVue® Jade (Abs max=478 nm and Em max=508 nm), and CellVue® Red (Ex max=567 nm and Em max=588 nm). In one embodiment, the fluorophore is CellVue® Maroon. In another embodiment, the fluorophore is CellVue® Claret. In yet another embodiment, the fluorophore is CellVue® Plum. In one embodiment, the fluorophore is CellVue® Burgundy. In another embodiment, the fluorophore is CellVue® Lavendar. In yet another embodiment, the fluorophore is CellVue® NIR815. In one embodiment, the fluorophore is CellVue® NIR780. In another embodiment, the fluorophore is CellVue® Jade. In yet another embodiment, the fluorophore is CellVue® Red.

In one embodiment described herein, a method for imaging a site of arthritis in an animal is provided. In various embodiments, the arthritis is an inflammatory arthritis. In some embodiments, the arthritis is selected from the group consisting of rheumatoid arthritis, osteoarthritis, psoriatic arthritis, traumatic arthritis, bacterial arthritis, post-infectious arthritis, lyme disease (Borreliose), anklyosing spondylilitis, and rubella arthritis. In one embodiment, the arthritis is rheumatoid arthritis. In anther embodiment, the arthritis is osteoarthritis. In yet another embodiment, the arthritis is psoriatic arthritis. In one embodiment, the arthritis is traumatic arthritis. In anther embodiment, the arthritis is bacterial arthritis. In yet anther embodiment, the arthritis is post-infectious arthritis. In one embodiment, the arthritis is lyme disease (Borreliose). In anther embodiment, the arthritis is anklyosing spondylilitis. In yet another embodiment, the arthritis is rubella arthritis.

In various embodiments, the imaging is optical imaging. As used herein, the term "optical imaging" refers to any method that forms an image for detection, staging or diagnosis of disease, follow up of disease development or for follow up of disease treatment based on interaction with light in the green to near-infrared region (wavelength 500-1200 nm). Optical imaging further includes all methods from direct visualization without use of any device and involving use of devices such as various scopes, catheters, and optical imaging equipment (e.g., computer-assisted hardware for tomographic presentations). The modalities and measurement techniques include, but are not limited to: luminescence imaging, endoscopy, fluorescence endoscopy, optical coherence tomography, transmittance imaging, time resolved transmittance imaging, confocal imaging, nonlinear microscopy, photoacoustic imaging, acousto-optical imaging, spectroscopy, reflectance spectroscopy, interferometry, coherence interferometry, diffuse optical tomography and fluorescence mediated diffuse optical tomography (continuous wave, time domain and frequency domain systems), and measurement of light scattering, absorption, polarization, luminescence, fluorescence lifetime, quantum yield, and quenching. Further details of these techniques are provided by: Tuan Vo-Dinh (editor): "Biomedical Photonics Handbook" (2003), CRC Press LCC; Mycek & Pogue (editors): "Handbook of Biomedical Fluorescence" (2003), Marcel Dekker, Inc.; Splinter & Hopper: "An Introduction to Biomedical Optics" (2007), CRC Press LCC.

In various embodiments, the animal is a mammal. The term "mammal" is well known to those of skill in the art. In one embodiment, the animal is a human.

In various embodiments, the site of arthritis to be imaged is selected from the group consisting of hand, foot, knee, elbow, shoulder, hip, and sacroiliac joint. In one embodiment, the site of arthritis is a hand (including all joints of the hand, such as the metacarpal interphalangeal joints). In another embodiment, the site of arthritis is a foot (including all joints of the foot, such as the metatarsal interphalangeal joints). In yet another embodiment, the site of arthritis is a knee. In one embodiment, the site of arthritis is an elbow. In another embodiment, the site of arthritis is a shoulder. In yet another embodiment, the site of arthritis is a hip. In one embodiment, the site of arthritis is a sacroiliac (lower back) joint.

In various embodiments, the site of arthritis to be imaged is an arthritic joint tissue. In other embodiments, the site of arthritis to be imaged is a joint. In some embodiments, the joint is selected from the group consisting of wrist, knee, elbow, forefoot, ankle, subtalar, and synovial joints. In one embodiment, the joint is a wrist joint. In another embodiment, the joint is a knee joint. In yet another embodiment, the joint is an elbow joint. In one embodiment, the joint is a forefoot joint. In another embodiment, the joint is an ankle joint. In yet another embodiment, the joint is a subtalar joint. In another embodiment, the joint is a synovial joint. In some embodiments, the site of arthritis at the arthritic joint tissue comprises pannus tissue.

In various embodiments, the population of cells is associated with arthritis. In some embodiments, the cells are selected from the group consisting of lymphocytes, macrophages, T cells, B cells, natural killer (NK) cells, myeloid cells, fibroblasts, synovial fibroblasts, endothelial cells, mature granulocytes, and neutrophils. In one embodiment, the cells are lymphocytes. In another embodiment, the cells are macrophages. In one embodiment, the cells are T cells. In one embodiment, the cells are B cells. In one embodiment, the cells are natural killer (NK) cells. In another embodiment, the cells are myeloid cells. In yet another embodiment, the cells are fibroblasts. In one embodiment, the cells are synovial fibroblasts. In another embodiment, the cells are endothelial cells. In yet another embodiment, the cells are mature granulocytes. In another embodiment, the cells are neutrophils.

In some embodiments, the cells express a cell surface marker selected from the group consisting of CD11b, CD19, GR-1, CD31, CD55, and F480. In one embodiment, the cells express a cell surface marker wherein the surface marker is CD11b. In another embodiment, the cells express a cell surface marker wherein the surface marker is CD19. In yet another embodiment, the cells express a cell surface marker wherein the surface marker is GR-1. In one embodiment, the cells express a cell surface marker wherein the surface marker is CD31. In another embodiment, the cells express a cell surface marker wherein the surface marker is CD55. In yet another embodiment, the cells express a cell surface marker wherein the surface marker is F480. In another embodiment, the cells are positive for both CD11b and Gr-1 surface markers.

Suitable dosages of the nanovesicles can be determined by standard methods, for example by establishing dose-response curves in laboratory animal models or in clinical trials. In various embodiments described herein, the dosage of the nanovesicles can vary significantly depending on the animal. Illustratively, suitable dosages of nanovesicles (administered in a single bolus or over time) include from about 1 ng/kg to about 10 mg/kg, from about 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses can range from about 0.01 µg to about 1000 mg per dose, from about 1 µg to about 100 mg per dose, or from about 100 µg to about 50 mg per dose, or from about 500 µg to about 10 mg per dose, or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose.

The size of the nanovesicles can also vary according to the present disclosure. In some embodiments, the average diameter of the nanovesicles may range from about 10 nanometers (nm) to about 1000 nm in diameter. In other embodiments, the average diameter of the nanovesicles may range from about 25 nm to about 500 nm. In other embodiments, the average diameter of the nanovesicles may range from about 50 nm to about 350 nm. In other embodiments, the average diameter of the nanovesicles may range from about 50 nm to about 250 nm. In other embodiments, the average diameter of the nanovesicles may range from about 50 nm to about 200 nm. In other embodiments, the average diameter of the nanovesicles may range from about 50 nm to about 150 nm. In other embodiments, the average diameter of the nanovesicles may range from about 50 nm to about 100 nm. In other embodiments, the average diameter of the nanovesicles is approximately 10 nm. In other embodiments, the average diameter of the nanovesicles is approximately 25 nm. In other embodiments, the average diameter of the nanovesicles is approximately 50 nm. In other embodiments, the average diameter of the nanovesicles is approximately 75 nm. In other embodiments, the average diameter of the nanovesicles is approximately 100 nm. In other embodiments, the average diameter of the nanovesicles is approximately 150 nm. In other embodiments, the average diameter of the nanovesicles is approximately 200 nm.

The size of the nanovesicles can be adjusted, if desired, by a variety of procedures including, for example, shaking, microemulsification, vortexing, extrusion, filtration, sonication, homogenization, repeated freezing and thawing cycles, extrusion under pressure through pores of defined size, or similar methods known to those skilled in the art.

In another embodiment described herein, a method for detecting early onset of arthritis in an animal is provided. As used herein, the term "early onset" refers to the form of arthritis that develops during the initial stages of disease, and may or may not include symptoms of arthritis. The previously described embodiments of arthritis, imaging, animals, sites of arthritis, populations of cells, and cell surface markers are applicable to the method for detecting early onset of arthritis in an animal described herein.

In another embodiment described herein, a method for assessing disease progression of arthritis in an animal is provided. Assessment of disease progression of arthritis is well known to one skilled in the art and may include assessment of the following: number of swollen joints, number of tender joints, bony swelling, effusion, syovitis/ soft tissue swelling, circumference, tenderness/pain, range of motion, alignment, active crepitus, warmth, erythema, instability, and the like. The previously described embodiments of arthritis, imaging, animals, sites of arthritis, populations of cells, and cell surface markers are applicable to the method for assessing inflammation of a joint in an animal.

In some embodiments, the assessment of disease progression of arthritis is used to determine arthritis treatment for the animal. In some embodiments, the assessment of disease progression of arthritis is used to monitor therapeutic response of arthritis treatment to the animal. Arthritis treatment for animals are well known in the art, including but not limited to acetaminophen, nonsteroidal anti-inflammatory drugs (NSAIDs), biologics, corticosteroids, disease-modifying anti-rheumatic drugs (DMARDs), immunosuppressants, and the like.

In another embodiment described herein, a method for assessing inflammation of a joint in an animal is provided. Assessment of inflammation of a joint in a patient is well known to one skilled in the art and may include assessment of the following: inflammatory cell infiltration, number of swollen joints, number of tender joints, bony swelling, effusion, syovitis/soft tissue swelling, circumference, tenderness/pain, range of motion, alignment, active crepitus, warmth, erythema, instability, and the like. The previously described embodiments of joints, imaging, animals, populations of cells, cell surface markers, determination of arthritis treatment, and monitoring therapeutic response of arthritis treatment are applicable to the method for assessing inflammation of a joint in an animal.

EXAMPLE 1

K/BxN Arthritis Model

Sera can be collected from KRN×NOD F1 mice, and 150 µl sera can be given by intraperitoneal injection to C57Bl/6J mice at day 0 of disease. Calipers can be used to measure paw thickness and ankle thickness in the mice. For ankle thickness, the elliptical area of mouse ankles can be calculated using internalleolar measurements and measurement of the area between the dorsal talus and calcaneus. In this arthritis model, 100% penetrance is normally observed, with animal hind paws being the most highly affected.

EXAMPLE 2

Collagen-Induced Arthritis (CIA) Model

DBA/1J male mice (eight weeks of age) can be injected intradermally at the base of the tail with 100 µg of bovine type II collagen (CII) (Elastin Products Co., Inc.) in complete Freund's adjuvant (CFA) on day 1. The mice can be given a similar challenge on day 21 following the initial CII injection. Mice can be evaluated for macroscopic arthritis using an arthritic index macroscopic scoring system ranging from 0 to 4 (0=no detectable arthritis, 1=swelling and/or redness of paw or one digit, 2=two joints involved, 3=three joints involved and 4=severe arthritis of the entire paw and digit). Compared to the K/BxN arthritis model, between 70-100% of mice in the CIA model develop overt arthritic disease and various joints will display arthritic disease.

EXAMPLE 3

Imaging of Nanoparticles Labeled with CVM Using IVIS®

An aliquot of CellVue® Maroon (CVM, Molecular Targeting Technologies Inc., West Chester, Pa.) in ethanol can be mixed with phospholipid solvent for bath sonication preparation by the procedure as previously described (see Kaimal V et al., "Saposin C Coupled Lipid Nanovesicles Enable Cancer-Selective Optical and Magnetic Resonance Imaging," Mol Imaging Biol (2010) and Qi X, "Cancer-selective targeting and cytotoxicity by liposomal-coupled lysosomal saposin C protein," Clin Cancer Res, 15: 5840-5851 (2009). Nanovesicles labeled with CVM can be separated from free CVM dye using a Sephadex™ G25 column (PD-10, Amersham Pharmacia Biotech, Piscataway, N.J.). Nanovesicles labeled with CVM (SapC=4.2 mg/kg, DOPS=2 mg/kg, CVM=6 µmol) and control agents can be administered to mice i.p or via tail vein injection in a volume of 200 µL. Real-time live images can be taken using an IVIS 200 Series imaging system with an XFO-6 fluorescent kit and quantified using Living Image software (Xenogen, Alameda, Calif.). Average radiance values (IVIS® intensity) of designated elliptical areas of the front and hind paws of the mice can be determined and the mean values between groups can be compared.

EXAMPLE 4

Analysis of Cells Using Flow Cytometry

To perform analysis of joint cells, mice can be sacrificed, paws can be removed above the ankle joint, skin can be dissected away, and the remaining tissue can be placed in 0.5 ml of RPMI. Using a number 10 scalpel blade and forceps, tissue can be separated from bones and joints and dissected/shredded as previously described (see Latham K A, "Ex vivo characterization of the autoimmune T cell response in the HLA-DR1 mouse model of collagen-induced arthritis reveals long-term activation of type II collagen-specific cells and their presence in arthritic joints," J Immunol 174: 3978-3985 (2005). Crude cell suspensions can be strained through a 70 micron cell strainer and cells can be counted. Approximately $1\times10^6$ cells can be stained in 100 µL of FACS buffer (1×PBS, 0.2% BSA) containing 10 µL of 2.4G2 (American Type Culture Collection) hybridoma supernatant. Three antibody panels can be assessed for cells from CIA treated mice as follows:

1. Panel 1=anti-CD4-FITC (clone GK1.5, BD Pharmingen, San Jose, Calif.), anti-CD8-Pacific Blue (clone 53-6.7, BD Pharmingen), and anti-CD19-PE (clone ID3, BD Pharmingen).

2. Panel 2=anti-CD11b-FITC (clone M1/70, BD Pharmingen), anti-CD11c-PE (clone HL3, BD Pharmingen), anti-Gr-1-AF700 (clone RB6-8C5, BD Pharmingen), and anti-F4/80-E450 (clone BM8, eBioscience).

3. Panel 3=anti-CD31-FITC (clone 390, BD Pharmingen) and anti-CD55-PE (clone RIKO-5, BD Pharmingen).

Three antibody panels can be assessed for cells from K/BxN treated mice as follows (clones as above):

1. Panel 1=anti-CD4-FITC, anti-CD8-Pacific Blue and anti-CD19-PE.

2. Panel 2=anti-CD11b-FITC, anti-CD11c-PE, and anti-Gr-1-E450.

3. Panel 3=anti-CD31-FITC, anti-CD55-PE and anti-F4/80-E450.

Cells can be acquired using a FACSCanto I RUO analytical cytometer and can be analyzed using FACSDiva software (Becton Dickinson, San Jose, Calif.).

EXAMPLE 5

Nanoparticles Localize and Accumulate for Visualization of Arthritic Joints by Fluorometric Imaging in K/BxN Arthritis Model The uptake of nanovesicles labeled with CVM was measured by optical imaging of mice in the K/BxN arthritis model described in Example 1. Mice challenged with K/BxN serum-transfer arthritis were examined for seven days following sera injection. Mice were administered nanovesicles labeled with CVM and exhibited robust CVM fluorescence in macroscopically arthritic paws as compared to arthritic paws in mice not administered nanovesicles labeled with CVM (see FIG. 1A). Mice not treated with sera did not develop arthritis and thus did not exhibit detectable CVM signal.

Mice challenged with K/BxN sera and receiving DOPS-CVM alone (i.e., without saposin C conjugation) did not exhibit detectable signal, although arthritis was macroscopically apparent (see FIG. 1B). Accordingly, saposin C conjugation to DOPS-CVM appears to be important for localization of CVM signal to arthritic paws. In comparison, administration of CVM alone (i.e., without saposin C or DOPS) also resulted in no detectable signal (data not shown).

EXAMPLE 6

Figure 2:
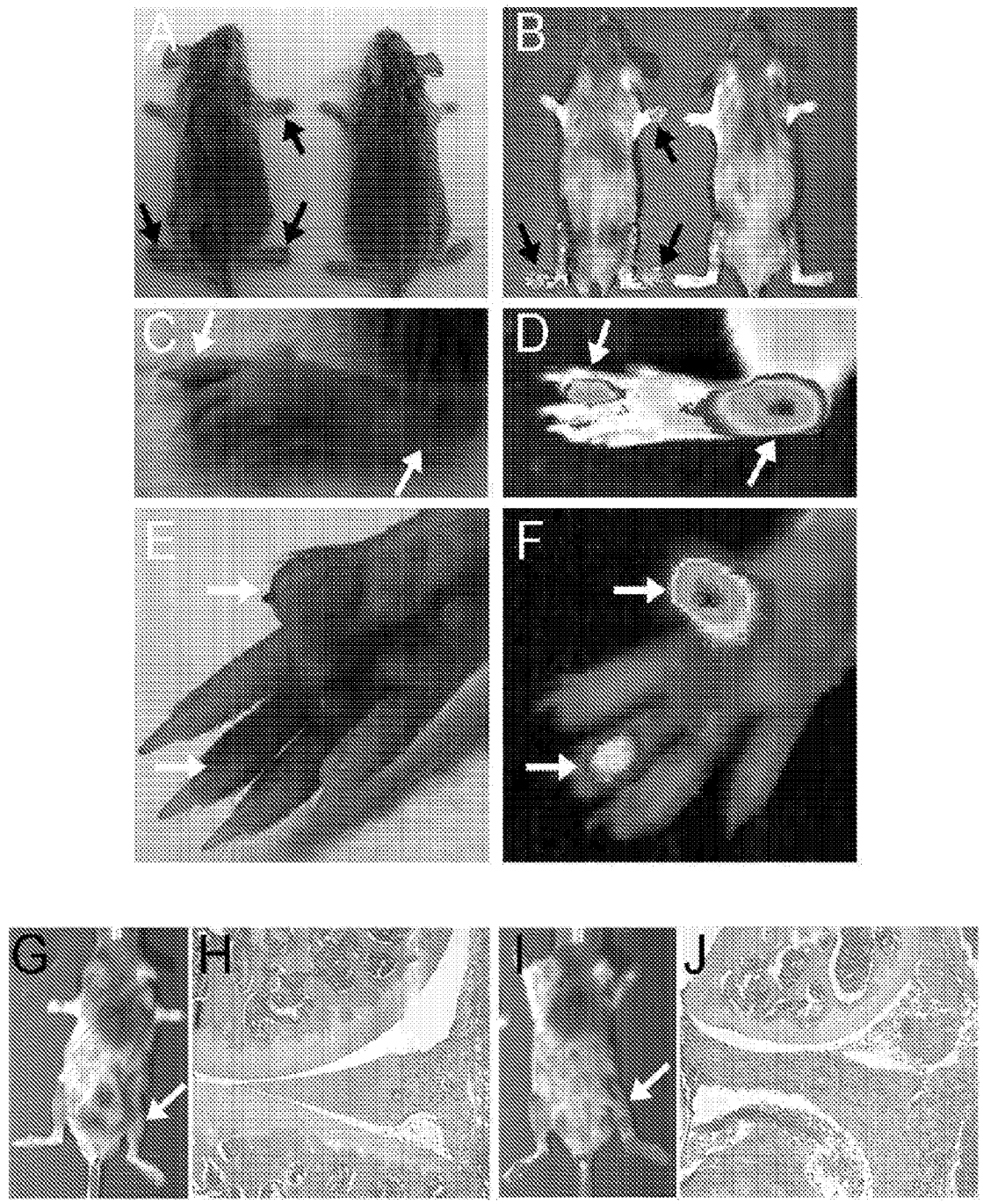
FIG. 2 shows that nanovesicles labeled with CVM localize to arthritic joints in a CIA model. (A) Light images of DBA/1 mice treated with collagen (left, CIA) and non-collagen treated (right, Control). (B) IVIS® images of mice in A, 24 hours following i.v. injection of SapC-DOPS-CVM. Light images of CIA hind paw (C) and forepaw (E) with corresponding IVIS® images in (D) and (F). Solid black arrows indicate macroscopically swollen paws and white arrows indicate macroscopically swollen joints. CVM intensity as measured by fluorometric imaging is represented by red, yellow, green, blue colorimetric scale with red representing highest and blue representing lowest intensity. (G) Mice knees that did not exhibit fluorescence. (H) Mice knees that did not exhibit fluorescence showed little arthritic knee joint pathology. (I) Mice knees that did exhibit fluorescence. (J) Mice knees that did exhibit fluorescence showed marked arthritic pathology, including abundant infiltration of inflammatory cells and synovial hyperplasia.

Nanoparticles Localize and Accumulate for Visualization of Arthritic Joints by Fluorometric Imaging in CIA Model The targeting of arthritic tissue by nanovesicles labeled with CVM was further assessed by examining localization in mice challenged with CIA (a well-characterized of murine models of inflammatory joint disease; see Example 2). A cohort of DBA/1J mice (see Example 1) was challenged and macroscopic disease was apparent 28 days following primary CII injection. Mice exhibiting macroscopically apparent arthritis also displayed localization of nanovesicles labeled with CVM accumulation as determined by IVIS® imaging specifically in macroscopically arthritic, but not non-arthritic paws 28 days following primary CII injection (see FIG. 2). In mice that did not receive CII (Controls, see FIGS. 2A and 2B) nanovesicles labeled with CVM IVIS® signal was not detected.

Furthermore, images focused on paws with arthritic digits (see FIGS. 2C-2F) indicated that nanovesicles labeled with CVM selectively accumulated to high levels in individual digits of a paw that were swollen, but not to those that were free of macroscopic evidence of disease (see swollen ankle and digit in FIGS. 2C and 2D; see forepaw digits in FIGS. 2E and 2F).

Signal was also detected in knees of challenged mice (see FIG. 2B) compared to control mice (ie, not administered CII). Although knee joints were not accessible for clinical scoring, further analysis of shaven mice knees at day 28 after CII injection indicated that increased fluorescence of nanovesicles labeled with CVM was associated with arthritic knee joint histopathology.

Mice knees that did not exhibit uptake of nanovesicles labeled with CVM (i.e., did not exhibit fluorescence) is exemplified in FIG. 2G. These knees showed little arthritic knee joint pathology (see FIG. 2H), including a small amount of infiltrating inflammatory cells and limited synovial hyperplasia.

Mice knees that exhibited increased uptake of nanovesicles labeled with CVM are exemplified in FIG. 2I. These knees showed marked arthritic pathology (see FIG. 2J), including abundant infiltration of inflammatory cells and synovial hyperplasia.

EXAMPLE 7

Nanoparticle Targeting of Arthritic Joints Over Disease Course Correlates with Disease Severity in K/BxN Arthritis Model The kinetics of nanovesicle accumulation in mice during the course of arthritic disease can be determined, particularly the correlation of signal intensity with severity of disease using the localization of nanovesicles labeled with CVM over time. The K/BxN arthritis model can be used to assess nanovesicle uptake and accumulation was assessed over time, beginning with disease initiation and continuing through the peak of disease severity.

Figure 3A:
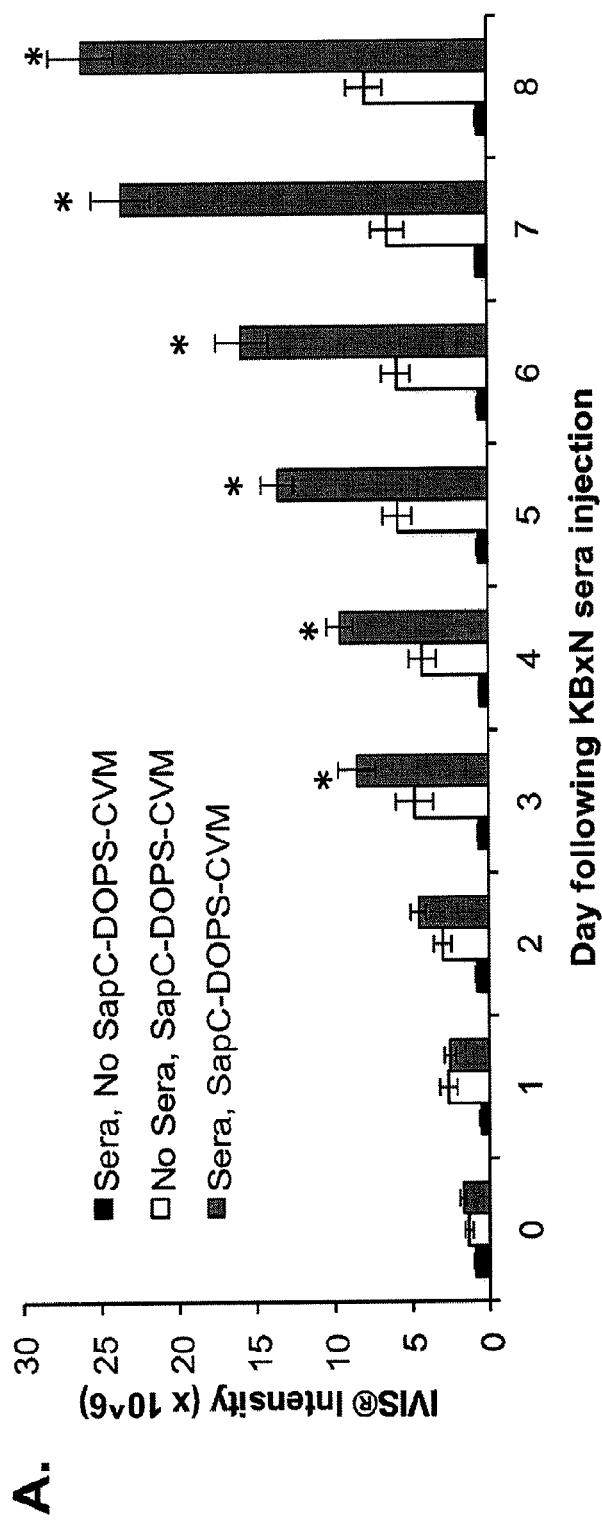
FIG. 3 shows that the intensity of imaging from nanovesicles labeled with CVM increases during the course of K/BxN arthritis and that CVM intensity correlates with arthritic parameters. C57Bl/6 mice (male and female) were administered 200 µL of K/BxN sera (i.p.) and 84 micrograms (µg) of SapC-DOPS-CVM as indicated. (A) Means of back paw intensity values are graphed as columns with error bars representing standard error of the mean. (* $p<0.05$ Sera, SapC-DOPS-CVM group vs. No Sera, SapC-DOPS-CVM group at days 3-8 following K/BxN sera injection). For mice treated with K/BxN sera (n=7) and administered SapC-DOPS-CVM, the changes in ankle circumference (B) and changes in paw thickness (C) were rounded to the nearest indicated number and graphed relative to the means of IVIS® signal intensity. Lines represent linear regression of values in (B) and (C) with respective correlation coefficients indicated. Correlation of arthritis parameters and IVIS® intensity signals in (B) and (C) are significant ($p<0.005$, as determined by Pearson Product Moment Correlation and Spearman Rank Order Correlation).

First, K/BxN sera were administered to C57Bl/6 mice and animals were imaged by IVIS® six hours later and then daily. Nanovesicles labeled with CVM were administered every other day, beginning at the initial sera administration. Average radiance values (IVIS® intensity) of designated elliptical areas of the hind paws were determined and the mean values of groups for each day (see FIG. 3A).

In K/BxN sera-challenged mice injected with nanovesicles labeled with CVM, steady and significant increases were observed in intensity of CVM signal (see FIG. 3A), with highest intensity at day 8 following K/BxN sera administration. Control mice receiving K/BxN sera but no nanovesicles labeled with CVM had low CVM signal (background radiance) that did not change throughout the analysis period, despite robust arthritic disease development. Control mice receiving nanovesicles labeled with CVM every other day, but not K/BxN sera, showed a slow increase in fluorescent signal intensity, indicating that with multiple injections of agent a marginal background accumulation of the agent within the paws exists that quickly plateaued.

Figure 3B:
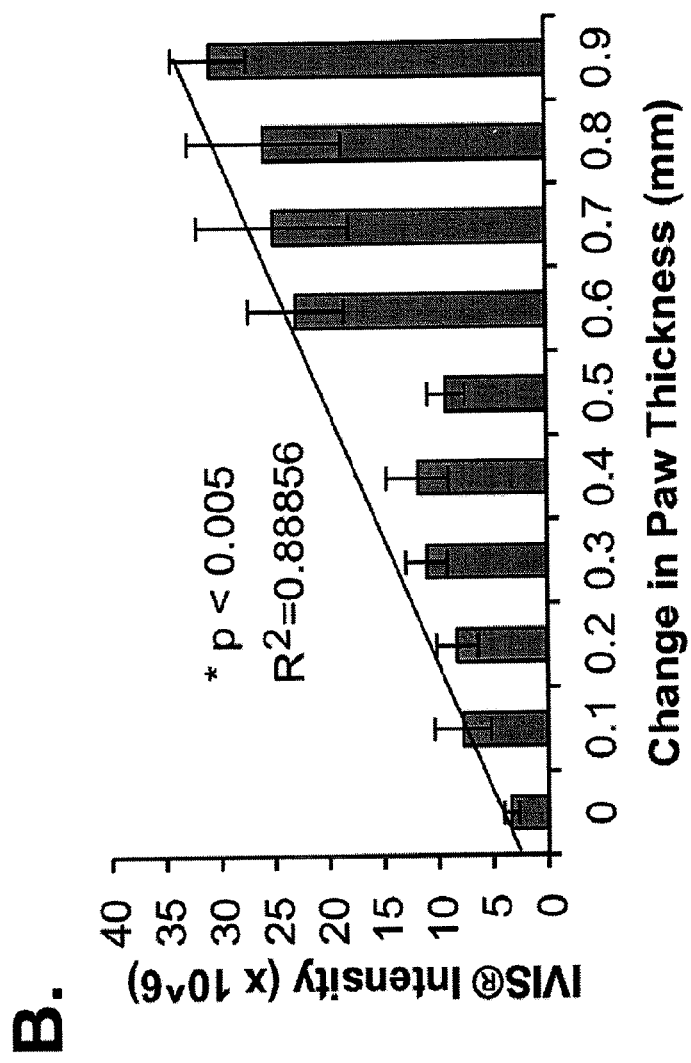
Figure 3C:
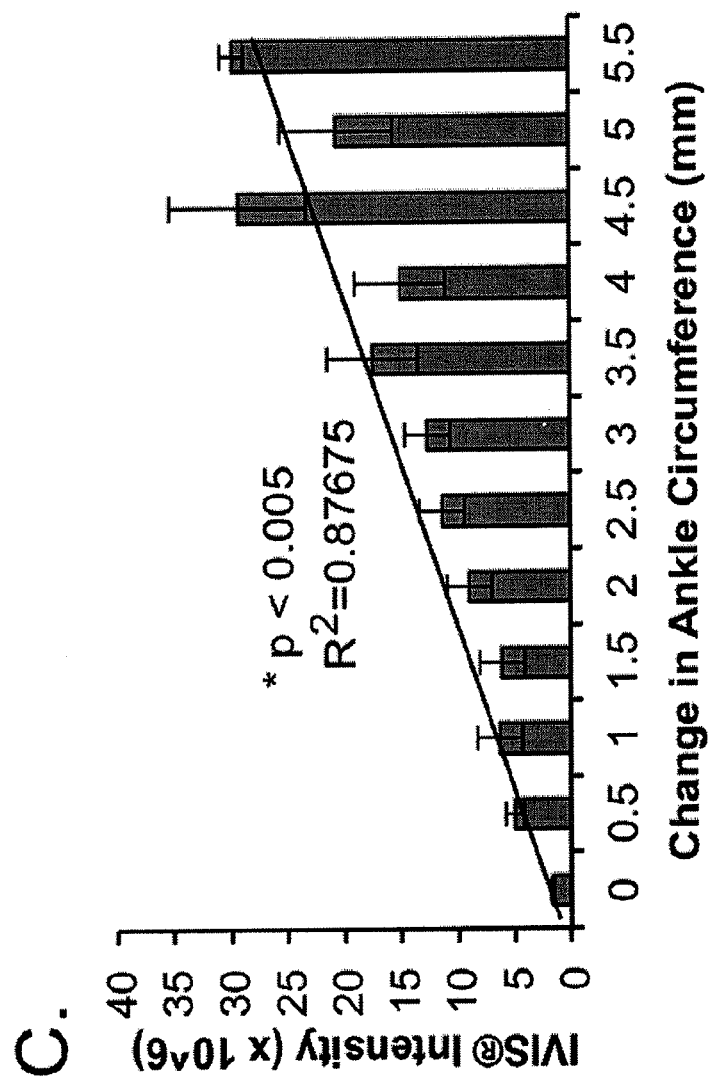

Paws of mice exhibiting higher positive changes in paw thickness and ankle circumference as measurements of arthritic severity exhibited higher levels of localization of nanovesicles labeled with CVM, as indicated by IVIS® intensity (see FIG. 3B and FIG. 3C, respectively). These data suggest that increases in arthritic severity as assessed by quantitative clinical arthritic measurements significantly correlate with increases in localization of nanovesicles to arthritic joints in the K/BxN model of arthritis.

EXAMPLE 8

Figure 4A:
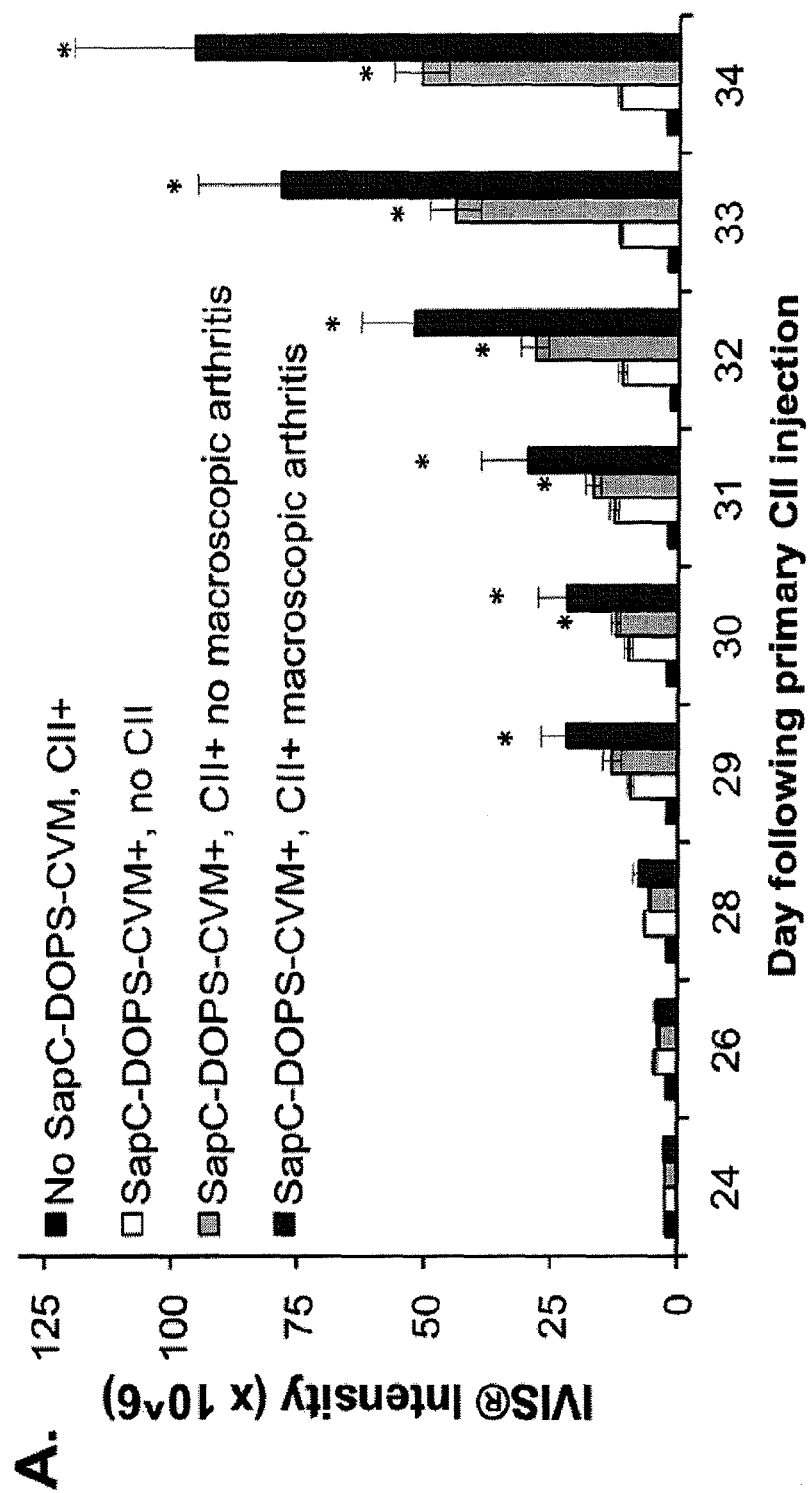
FIG. 4 shows that intensity of IVIS® signal from mice challenged with CII increases over time-course of disease and correlates with arthritic severity. (A) Mice were injected i.p. with SapC-DOPS-CVM starting on day 23 following primary CII immunization and then every other day. Mice were imaged daily by IVIS®. Columns indicate the mean IVIS® intensity values (average radiance) for each group (+/−SEM). Mice were scored macroscopically for arthritis daily. The number of paws imaged in the various groups are as follows: No SapC-DOPS-CVM, CII+: 16; SapC-DOPS-CVM+, no CII:16; SapC-DOPS-CVM+, CII+macroscopic arthritis: 8; SapC-DOPS-CVM+CII+no apparent arthritis: 24. (*=$p<0.05$ as compared to SapC-DOPS-CVM+, no CII. SapC-DOPS-CVM, CII+ compared to SapC-DOPS-CVM, No CII: $p<0.05$ days 29-34). (B) Box plots indicate the median values and range for IVIS® intensity of paws receiving the specified arthritic score during the time course of arthritic disease. The line represents linear regression of mean values, with the respective correlation coefficients indicated. Correlation of arthritis parameter values and IVIS® intensity signal values is significant ($p<0.005$).

Nanoparticle Targeting of Arthritic Joints Over Disease Course Correlates with Disease Severity in CIA Model The CIA model can also be used to assess nanovesicle uptake and accumulation was assessed over time, beginning with disease initiation and continuing through the peak of disease severity. CII-challenged mice were administered nanovesicles labeled with CVM at day 23 and every other day thereafter. These mice were imaged daily from days 24-34 following CII primary immunization (see FIG. 4A). Similar to Example 7, paws from mice immunized with CII and injected with nanovesicles labeled with CVM demonstrated prominent CVM signal at day 28 that steadily increased over the course of disease.

Figure 4B:
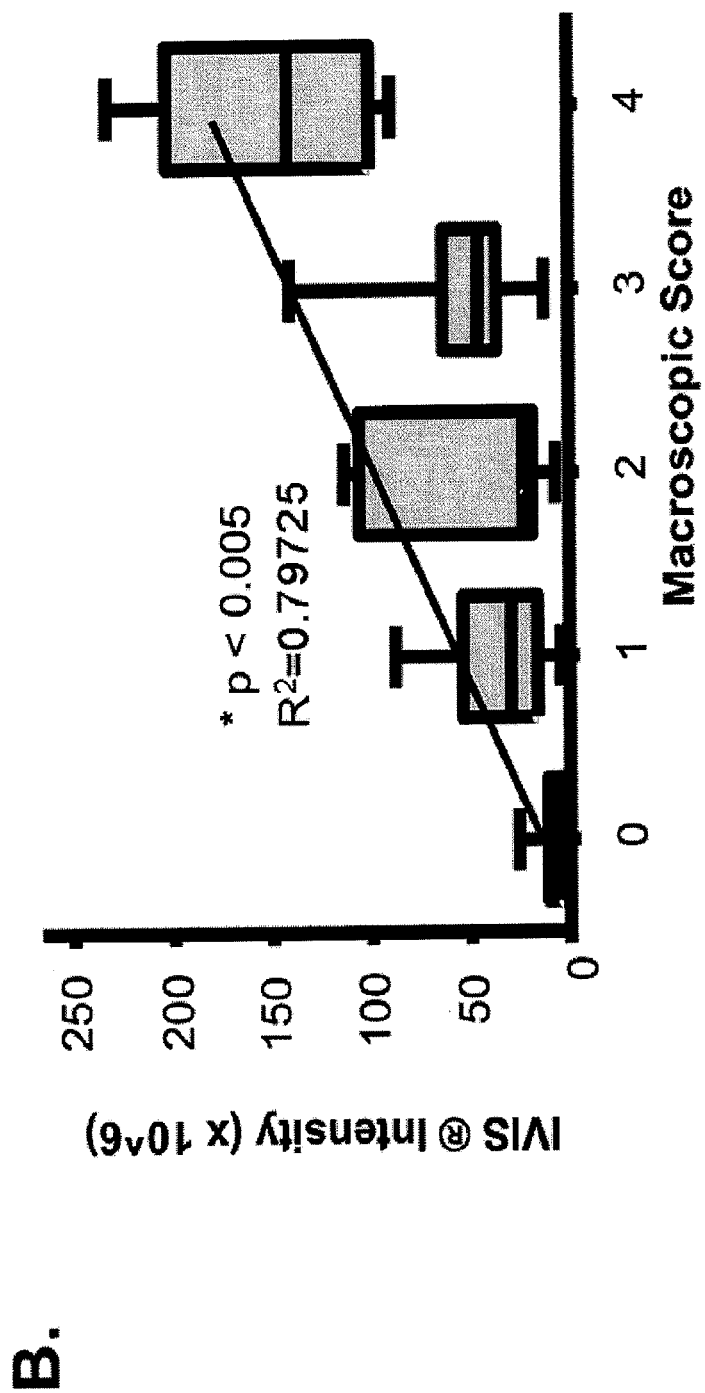

Furthermore, the repetitive treatment regime of nanovesicles labeled with CVM resulted in low-level accumulation of CVM signal in paws of mice receiving nanovesicles labeled with CVM alone (ie, without CII treatment), indicating background accumulation of the agent that was independent of disease pathogenesis. Fluorescent signal was not observed in paws of either control or arthritic mice that did not receive nanovesicles labeled with CVM. Paws from CIA-challenged mice receiving nanovesicles labeled with CVM that were overtly macroscopically arthritic demonstrated the highest fluorescent intensity, and arthritic scores showed a positive correlation with increases in CVM intensity (see FIG. 4B). Furthermore, paws from CIA-challenged mice, which were macroscopically scored as non-arthritic, also showed significant increases in CVM fluorescence intensity as compared to control mice (i.e., not treated with CII) (see FIG. 4A). This observation suggests that nanovesicles labeled with CVM may localize to joints with subclinical arthritis (i.e., early in the course of arthritis).

EXAMPLE 9

Nanoparticles are Detectable in Joint Cell Suspensions and Accumulate in Cells with Various Cell Surface Markers in K/BxN Arthritis Model Since nanovesicles labeled with CVM localize specifically to arthritic joints, the cell types targeted by nanovesicles labeled with CVM can be evaluated. Cells extracted from joints were stained with labeled antibodies to cell-surface markers on lymphocytes (T cells: CD4, CD8; B cells: CD19), myeloid cells (CD11b, CD11c, Gr-1 and F4/80), endothelial cells (CD31), and synovial fibroblasts (CD55high).

Figure 5A:
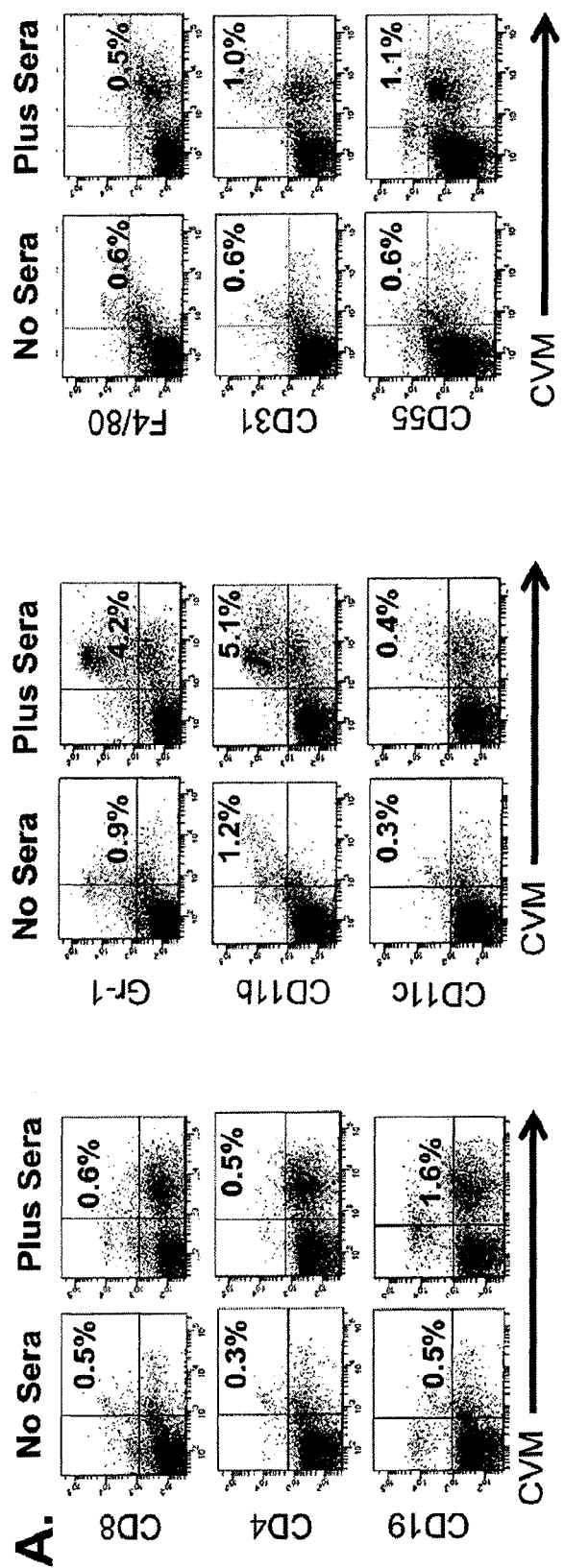
FIG. 5 shows that nanovesicles labeled with CVM target CD11b+ and/or Gr-1+ joint cells in the K/BxN model of arthritis. Joint cells from hind paws were stained with antibodies to cell surface markers as indicated. FACS plots are representative from one animal, with bar graphs indicating the means (+/−SEM) of groups. (A) Dot plots indicate cell populations that are CVM positive and positive for other cell surface markers. (B) CVM+ cells. Columns represent mean of total cells that are CVM+ (+/−SEM) with treatment of animals as indicated. (*=$p<0.05$). (C) Bar graph indicates means (+/−SEM) of the percentage of total cells that are CVM+ and positive for the indicated cell surface marker. (*=$p<0.05$). (D) Dot plots show forward (FSC) and side scatter (SSC) for joint populations with gating for CVM+ cell populations versus side scatter (SSC). Gated CVM+ cells were further analyzed for specific cell-surface markers CD11b, CD11c and Gr-1 with percentages indicated. (E) Columns represent the mean (+/−SEM) of the percentage of total cells that are positive for CVM, CD11b, and also positive for either CD11c or Gr-1 (*=$p<0.05$). (N=4 No Sera, SapC-DOPS-CVM; N=9 Sera, SapC-DOPS-CVM).
Figure 5B:
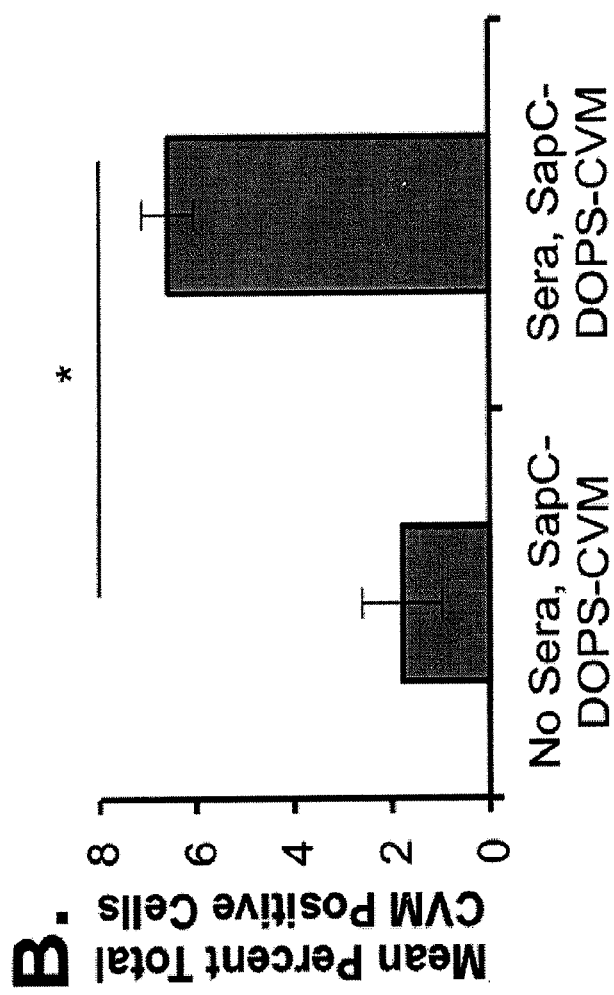

At day nine following sera administration in the K/BxN arthritis model, mice were sacrificed and single cell suspensions were obtained from back paws of individual mice. Analysis of joint cells from mice administered nanovesicles labeled with CVM demonstrates an increase in the CVM+ joint cells upon sera treatment (see, e.g., FIGS. 5A and 5B). For example, an average of ~6-7% of the isolated live-gated joint cells were positive for CVM, compared to only 1% of the cells staining positive for CVM in control cells (ie, not given KBxN sera) (see FIG. 5B).

Figure 5C:
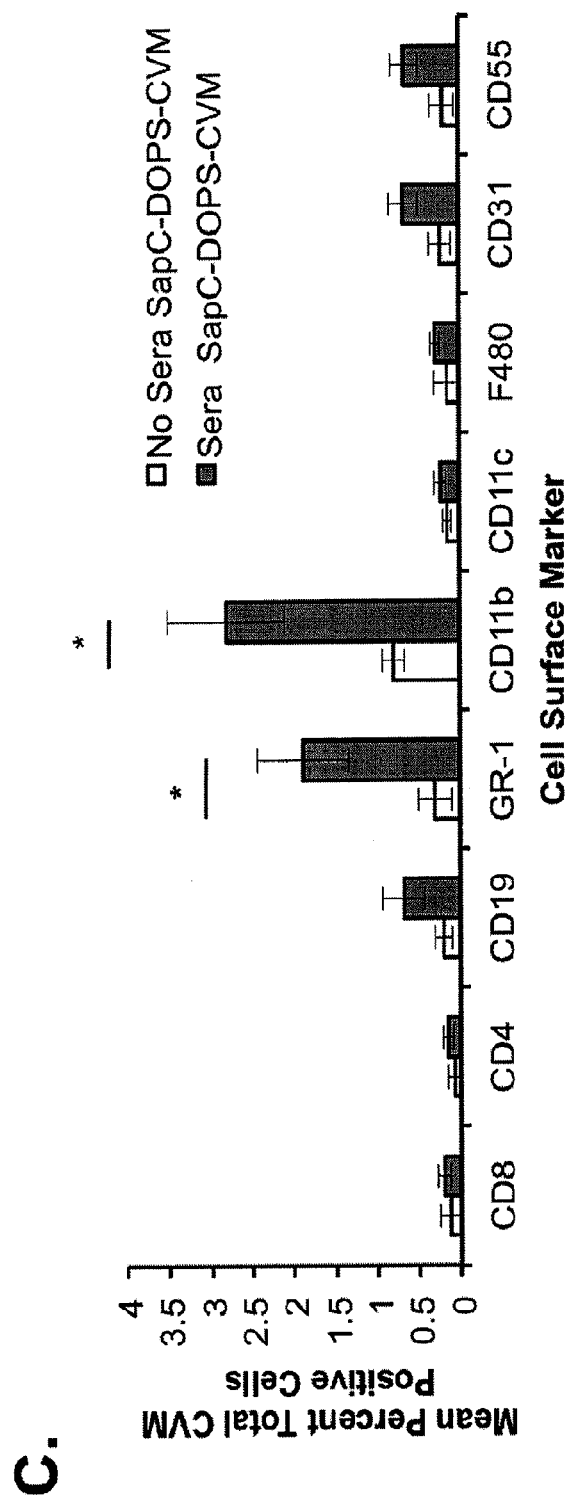
Figure 5D:
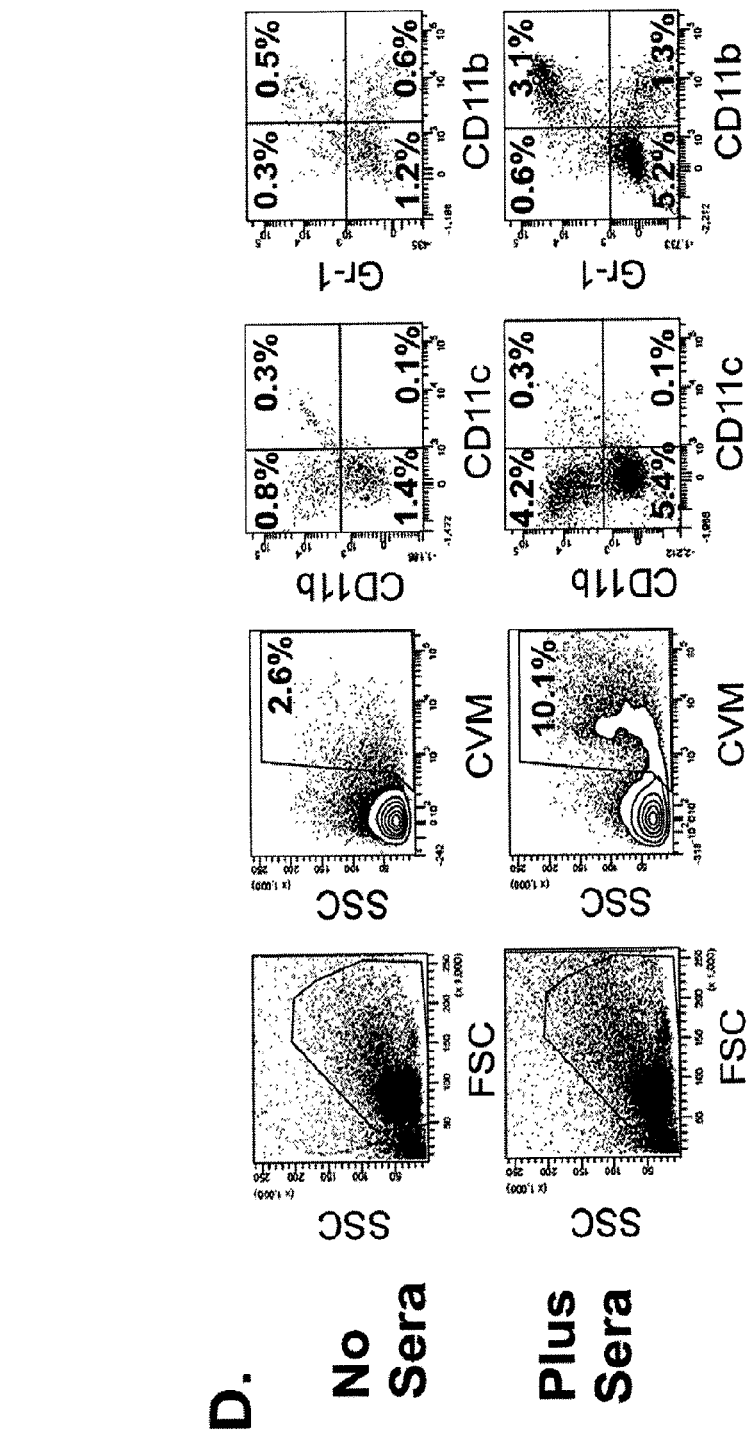
Figure 5E:
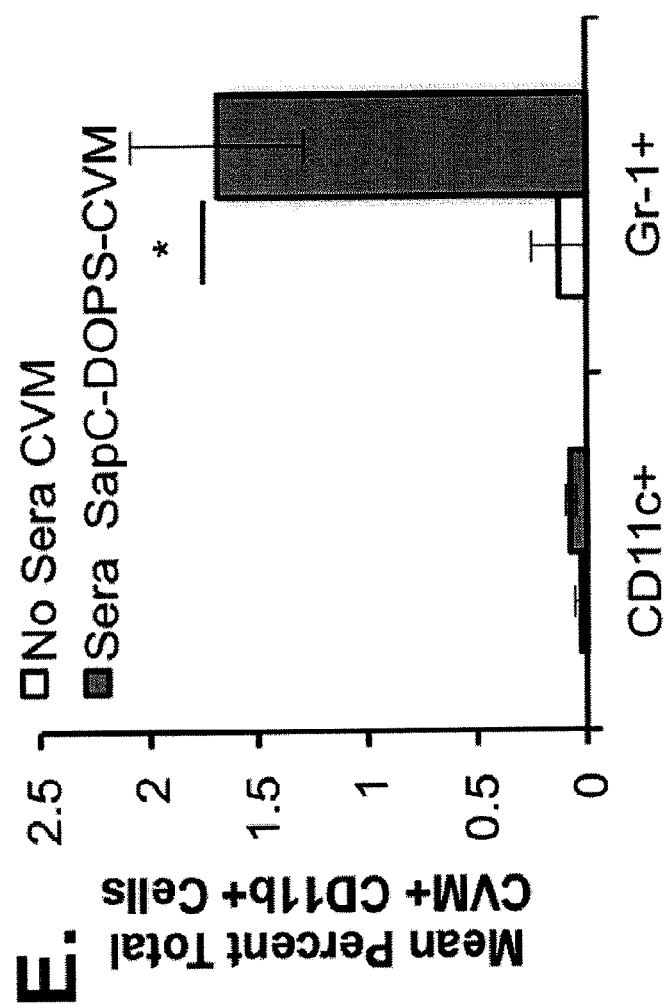

The majority of cells to which CVM localizes also stained positively for the myeloid markers Gr-1 (mean=1.9%, ranging from 0.2%-4.5%) and CD11b (mean=2.8%, ranging from 1.1%-6.0%) (see FIG. 5C). Further analysis of the 6-7% SapC-DOPS-CVM positive cells for co-expression of cell surface markers indicates that approximately one-third express both CD11b and Gr-1 (mean=1.7%, ranging from 0.5%-3.2%), which is consistent with a neutrophil phenotype (see FIG. 5E). None of the CVM+ cells stained positive for both Gr-1 and CD11c.

Additionally, the expression of CD19, CD31 and CD55 in cells treated with nanovesicles labeled with CVM trended to be higher in joint cells from mice treated with K/BxN sera compared to joint cells from control mice (see FIG. 5C).

The targeting of nanovesicles labeled with CVM to hind paws in the K/BxN arthritis model, with a direct correlation with paw thickness and ankle circumference and a specific correlation with CD11b+Gr-1+ cells, suggests the complete penetrance of the K/BxN arthritis model.

EXAMPLE 10

Nanoparticles are Detectable in Joint Cell Suspensions and Accumulate in Cells with Various Cell Surface Markers in CIA Model In the CIA model, back paws of mice were taken and joint cells were pooled for analysis. Mice were sacrificed 35 days following primary CII injection. Arthritic macroscopic scores were variable among the mice, with a median score of 1.5-2 for mice administered nanovesicles labeled with CVM or not administered nanovesicles labeled with CVM as a negative control. Disease incidence in mice treated with nanovesicles labeled with CVM and control mice (i.e., mice not administered nanovesicles labeled with CVM) was similar, with 63% (5/8 affected) and 50% (4/8 affected) with overt macroscopic disease, respectively. Cells extracted from joints were stained with labeled antibodies for lymphoid, myeloid, endothelial and synovial fibroblast cells as described above.

Figure 6A:
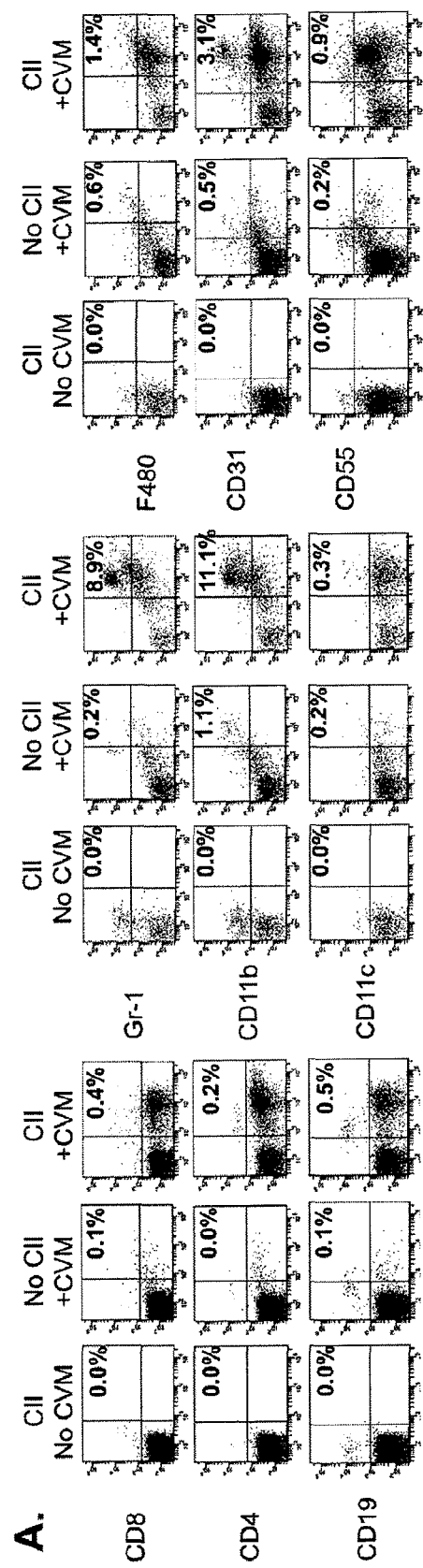
FIG. 6 shows that nanovesicles labeled with CVM target joint cells that are positive for CD19, Gr-1, CD11b, CD31, or CD55 in the CIA model of arthritis. Cells were stained with antibodies to cell surface markers as indicated. FACS plots are representative from one animal, with bar graphs indicating the means (+/−SEM) of groups. (A) Dot plots indicate cell populations that are CVM positive and positive for other cell surface markers. (B) CVM+ cells. Columns represent mean of total cells that are CVM+ (+/−SEM error bars) with treatment of animals as indicated. (*=$p<0.0001$). (C) Columns indicate means (+/−SEM error bars) of the percentage of total cells that are CVM+ and positive for the indicated cell surface marker. (*=$p<0.05$). (D) Dot plots show forward (FSC) and side scatter (SSC) for joint populations with gating for CVM+ cell populations versus side scatter (SSC). Gated CVM+ cells are further analyzed for combinations of the specific cell-surface markers CD11b, CD11c and Gr-1 as indicated. (E) Columns represent the mean (+/−SEM error bars) of the percentage of total cells that are positive for CVM, CD11b, and also positive for either CD11c or Gr-1. (N=4 No CII SapC-DOPS-CVM; N=8 CII+, SapC-DOPS-CVM+) (* $p<0.05$).
Figure 6B:
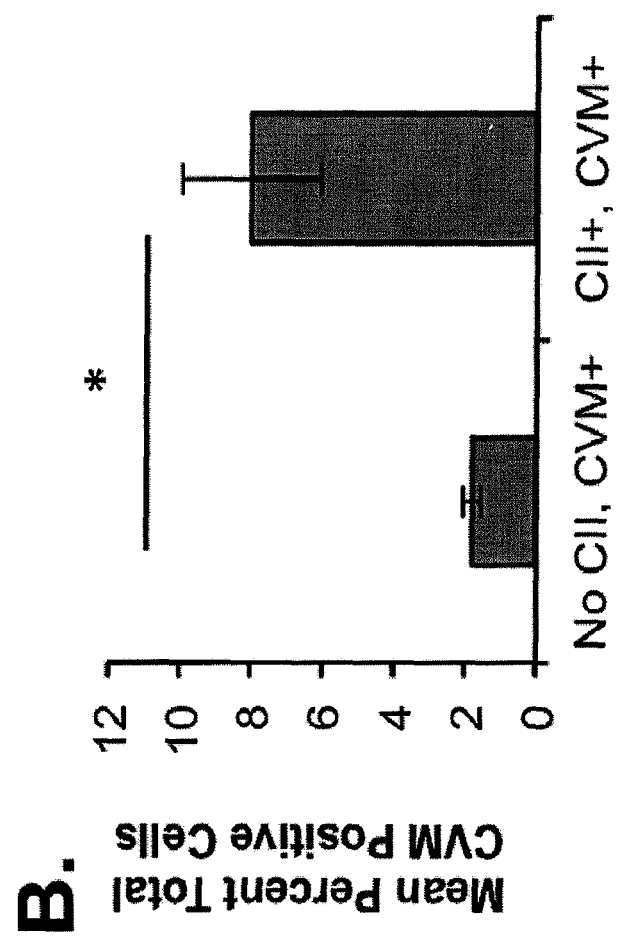
Figure 6C:
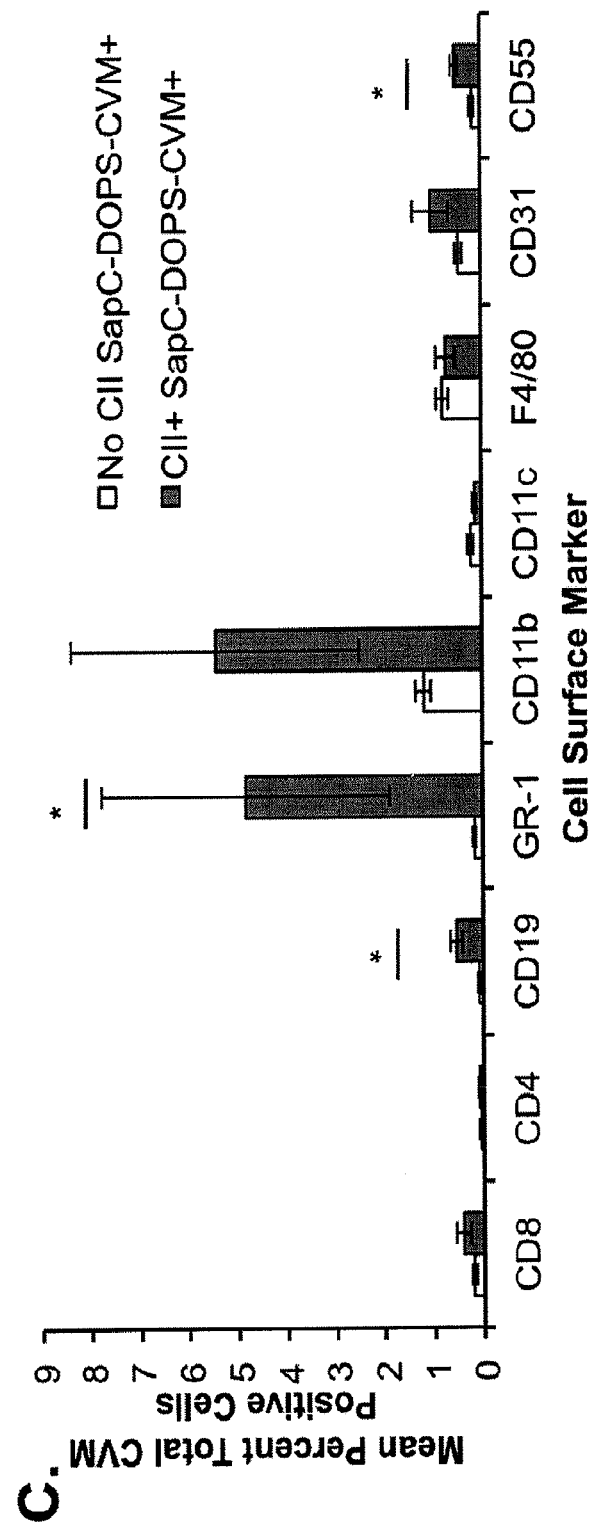
Figure 6D:
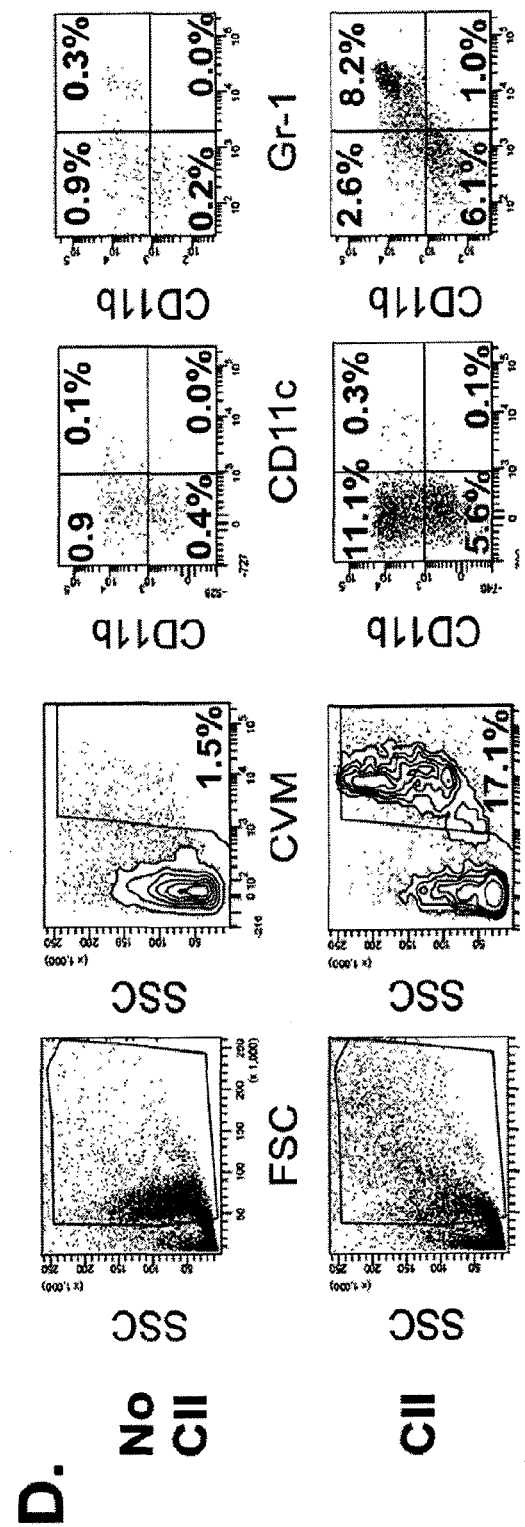
Figure 6E:
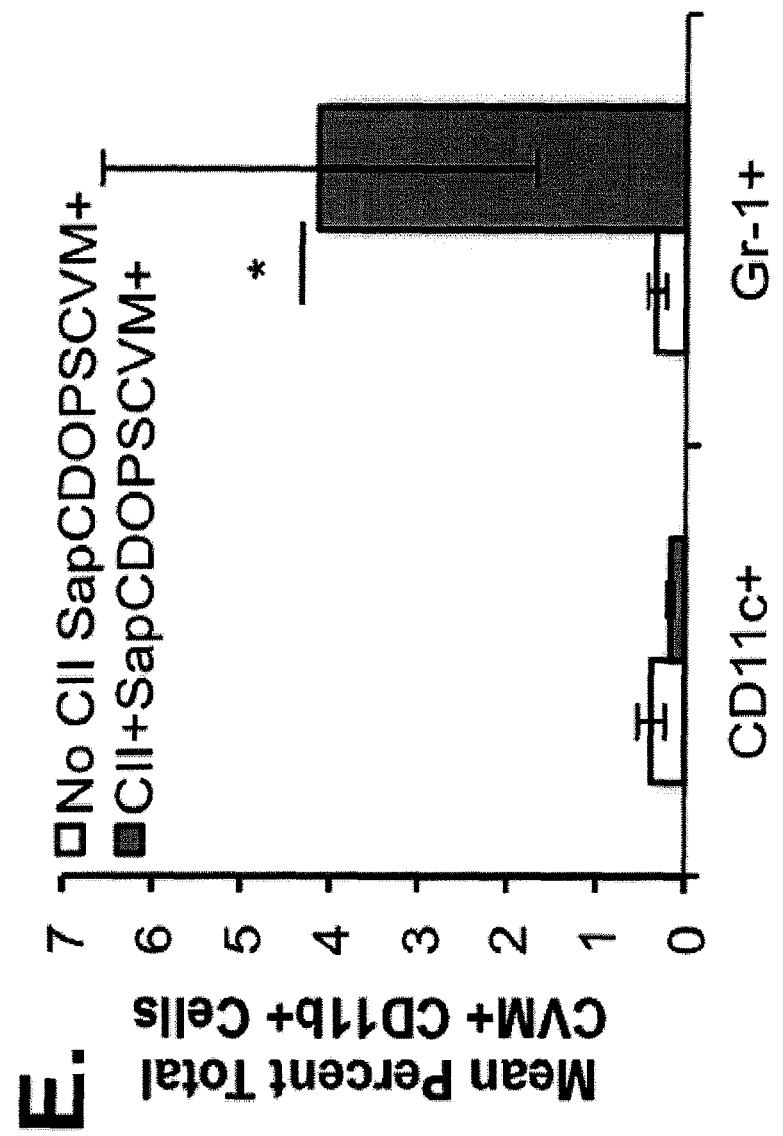

Joint cells from mice treated with nanovesicles labeled with CVM demonstrate an increase in CVM+ cells upon CII challenge with the mean percent of CVM+ joint cells averaging approximately 8% of live cells (see FIG. 6B). CII-challenged mice demonstrated populations that were positive for CD19, CD11b, CD55 and Gr-1, regardless of treatment with nanovesicles labeled with CVM (see dot plot analysis in FIG. 6). However, the majority of CVM+ cells from CIA mice and given nanovesicles labeled with CVM (CII, +CVM) were also positive for CD11b (mean=5.5%, range=0.5% to 24.3%) and Gr-1 (mean=4.8%, range 0.3% to 24.2%) (see FIG. 6C). CVM+ cell populations also stained positive for CD19 (range 0.2% to 1.3%), CD31 (range 0.3% to 3.1%) or CD55 (range 0.3 to 0.9%). FIG. 6D indicates the gating strategy for CVM+ populations, which were further analyzed for dual expression of specific cell surface markers. A significant portion of the nanovesicle-CVM+ cells (mean=5.4%, ranging from 0.3% to 20%) also expressed both CD11b and Gr-1 on their cell surface, but not CD11c (see FIG. 6E). Furthermore, CVM+ cells did not stain positive for both Gr-1 and CD11c. The variability in nanovesicle-CVM+ cell populations extracted from individual mice is consistent with the variability in the penetrance of disease as cells from both hind paws were pooled for cell analysis.

In the CIA model, a significant correlation between the observed intensity (following administration of nanovesicles labeled with CVM) and arthritic severity was observed, but more variability was observed in determination of cell types.

The invention claimed is:

1. A method for imaging a site of arthritis in an animal, the method comprising:
   administering to the animal a nanovesicle comprising saposin C, 1,2-dioleoyl-sn-glycero-3-phospho-L-serine (DOPS), and a fluorophore selected from the group consisting of a far-red fluorophore and a near-infrared fluorophore; and
   optically imaging the site of arthritis in the animal,
   wherein the site of arthritis is detected by imaging a population of cells expressing a cell surface marker selected from the group consisting of CD11b, CD19, GR-1, CD55, and F480 at the site of arthritis.

2. The method of claim 1, wherein detection of early onset of arthritis is obtained from the imaging of the population of cells.

3. The method of claim 1, wherein the arthritis is an inflammatory arthritis.

4. The method of claim 1, wherein the arthritis is rheumatoid arthritis.

5. The method of claim 1, wherein the animal is a human.

6. The method of claim 1, wherein the fluorophore is CellVue® Maroon (CVM).

7. The method of claim 1, wherein the cells are selected from the group consisting of lymphocytes, macrophages, T cells, B cells, natural killer (NK) cells, myeloid cells, fibroblasts, synovial fibroblasts, endothelial cells, mature granulocytes, and neutrophils.

8. The method of claim 1, wherein the cells are neutrophils.

9. A method for assessing disease progression of arthritis in an animal, the method comprising:
   administering to the animal a nanovesicle comprising saposin C, 1,2-dioleoyl-sn-glycero-3-phospho-L-serine (DOPS), and a fluorophore selected from the group consisting of a far-red fluorophore and a near-infrared fluorophore; and
   optically imaging a site of arthritis in the animal,
   wherein the site of arthritis is detected by imaging a population of cells expressing a cell surface marker selected from the group consisting of CD11b, CD19, GR-1, CD55, and F480 at the site of arthritis, and
   wherein the assessment of disease progression of arthritis is obtained from the imaging of the population of cells.

10. The method of claim 9, wherein the assessment of disease progression of arthritis is used to determine arthritis treatment for the animal.

11. The method of claim 9, wherein the assessment of disease progression of arthritis is used to monitor therapeutic response of arthritis treatment to the animal.

12. A method for assessing inflammation of a joint in an animal, the method comprising:
   administering to the animal a nanovesicle comprising saposin C, 1,2-dioleoyl-sn-glycero-3-phospho-L-serine (DOPS), and a fluorophore selected from the group consisting of a far-red fluorophore and a near-infrared fluorophore; and
   optically imaging a site of arthritis in the animal,
   wherein the inflammation of the joint is detected by imaging a population of cells expressing a cell surface marker selected from the group consisting of CD11b, CD19, GR-1, CD55, and F480 at the joint, and
   wherein the assessment of inflammation is obtained from the imaging of the population of cells.

13. The method of claim 12, wherein the assessment of inflammation is used to determine arthritis treatment for the animal.

14. The method of claim 12, wherein the assessment of inflammation is used to monitor therapeutic response of arthritis treatment to the animal.

* * * * *

SEQUENCE LISTING

<160> NUMBER OF SEQ ID NOS: 1

<210> SEQ ID NO 1
<211> LENGTH: 80
<212> TYPE: PRT
<213> ORGANISM: Homo sapiens

-continued

```
<400> SEQUENCE: 1

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45

Glu Val Val Asp Thr Tyr Gly Ser Ser Ile Leu Ser Ile Leu Leu Glu
    50                  55                  60

Glu Val Ser Pro Glu Leu Val Cys Ser Met Leu His Leu Cys Ser Gly
65                  70                  75                  80
```